(12) United States Patent
Harris et al.

(10) Patent No.: US 8,415,353 B2
(45) Date of Patent: Apr. 9, 2013

(54) AMINO-QUINOXALINE AND AMINO-QUINOLINE COMPOUNDS FOR USE AS ADENOSINE $A_{2a}$ RECEPTOR ANTAGONISTS

(75) Inventors: Joel M. Harris, Kenilworth, NJ (US); Bernard R. Neustadt, Kenilworth, NJ (US); Hong Liu, Kenilworth, NJ (US); Jinsong Hao, Kenilworth, NJ (US); Andrew W. Stamford, Kenilworth, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/920,928

(22) PCT Filed: Mar. 3, 2009

(86) PCT No.: PCT/US2009/035828
§ 371 (c)(1),
(2), (4) Date: Jan. 7, 2011

(87) PCT Pub. No.: WO2009/111442
PCT Pub. Date: Sep. 11, 2009

(65) Prior Publication Data
US 2011/0105513 A1    May 5, 2011

Related U.S. Application Data

(60) Provisional application No. 61/033,471, filed on Mar. 4, 2008.

(51) Int. Cl.
*A61K 31/495* (2006.01)
(52) U.S. Cl. ........ 514/249; 544/353; 548/131; 548/143; 548/159; 548/202; 548/364.7; 549/434
(58) Field of Classification Search .......... 514/249; 544/353; 548/131, 143, 159, 202, 364.7; 549/434
See application file for complete search history.

(56) References Cited

U.S. PATENT DOCUMENTS
4,254,123 A * 3/1981 Ramm et al. ........... 514/250

FOREIGN PATENT DOCUMENTS
WO    0255083    7/2002

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Wolff, Manfred E., Ed. Burger's Medicinal Chemistry and Drug Discovery—Fifth Edition, New York: John Wiley & Sons, 1996, 1, 975-976.*
Noblia, P, et al., Journal of Inorganic Biochemistry, vol. 100, No. 2, Feb. 1, 2006, pp. 281-287.
Vieites, M, et al., Journal of Inorganic Biochemistry, vol. 100, No. 8, Aug. 1, 2006, pp. 1358-1367.
Kiran, et al., Heterocyclic Communications, vol. 12, No. 6, 2006 pp. 481-484.
Charushin, et al., Mendeleev Communications, vol. 11, No. 2, Jan. 1, 2001, pp. 54-55.
Sharma, et al., Tetrahedron Ltrs., vol. 41, No. 18, 2000, pp. 3493-3495.
Montoya, et al., Il Farmaco, vol. 53, No. 8-9, 1998, pp. 570-573.
Monge, et al., Journal of Heterocyclic Chem., vol. 26, 1989, pp. 1623-1626.
Ukhov, et al., Chem. of Heterocyclic Compounds, vol. 24, No. 11, 1988, pp. 1256-1258.
Althuis, et al., J. Med. Chem., vol. 23, No. 3, 1980, pp. 262-269.
Taylor, et al., Journ. of the American Chem. Society, vol. 78, 1956, pp. 5108-5115.
Gowenlock, A., et al., Journal of the Chem. Society, Chem. Society, Letchworth, Jan. 1, 1948, pp. 517-519.
Rene Milcent, Ann. Chim., t. 2, 1967, No. 4, Contribution A L'etude Des Oxadiazoles 1, 3,4; pp. 221-226.

* cited by examiner

*Primary Examiner* — Douglas M Willis
(74) *Attorney, Agent, or Firm* — H. Eric Fischer; Gerard M. Devlin

(57) ABSTRACT

Compounds of the Formula (I), where W represents CH or N; and Q represents —CN, —C(=NOH)NH$_2$, —CONHR$^1$ or various herein described heterocyclic radicals; as well as pharmaceutically acceptable salts, solvates, esters and prodrugs thereof are adenosine $A_{2a}$ receptor antagonists and, therefore, are useful in the treatment of central nervous system diseases, in particular Parkinson's disease.

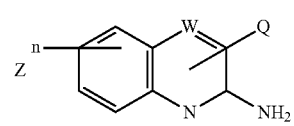

7 Claims, No Drawings

AMINO-QUINOXALINE AND AMINO-QUINOLINE COMPOUNDS FOR USE AS ADENOSINE $A_{2a}$ RECEPTOR ANTAGONISTS

BACKGROUND OF THE INVENTION

1. Field of the Invention

The present invention relates to amino-quinoxaline and amino-quinoline adenosine $A_{2a}$ receptor antagonist compounds, methods of using said compounds in the treatment of central nervous system diseases, in particular Parkinson's disease, and to pharmaceutical compositions comprising said compounds.

2. Description of Related Art

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2a}$, $A_{2b}$ and $A_3$. $A_1$ and $A_3$ are high-affinity, inhibiting the activity of the enzyme adenylate cyclase, and $A_{2a}$ and $A_{2b}$ are low-affinity, stimulating the activity of the same enzyme. Analogs of adenosine able to interact as antagonists with the $A_1$, $A_{2a}$, $A_{2b}$ and $A_3$ receptors have also been identified.

Selective antagonists for the $A_{2a}$ receptor are of pharmacological interest because of their reduced level of side effects. In the central nervous system, $A_{2a}$ antagonists can have antidepressant properties and stimulate cognitive functions. Moreover, data has shown that $A_{2a}$ receptors are present in high density in the basal ganglia, known to be important in the control of movement. Hence, $A_{2a}$ antagonists can improve motor impairment due to neurodegenerative diseases such as Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2a}$ affinity with varying degrees of $A_{2a}$ vs. $A_1$ selectivity. Triazolo-pyrimidine adenosine $A_{2a}$ receptor antagonists have been disclosed previously, for example in WO 95/01356; U.S. Pat. No. 5,565,460; WO 97/05138; WO 98/52568, WO 01/92264, PCT/US02/32630, filed Oct. 11, 2002, and U.S. Pat. No. 6,897,217.

Adenosine $A_{2a}$ receptor antagonists have been disclosed as being useful in the treatment or prevention of Extra Pyramidal Syndrome, dystonia, restless leg syndrome (RLS) or periodic limb movement in sleep (PLMS) in PCT/US03/40456, filed Dec. 17, 2003, and have been disclosed as being useful in the treatment of attention deficit hyperactivity disorder (ADHD) in WO 02/055083.

SUMMARY OF THE INVENTION

The present invention relates to compounds of the structural Formula I:

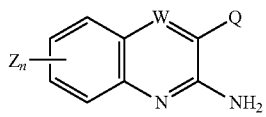

I wherein:

W represents CH or N;

Z represents hydrogen, halogen or haloalkyl;

n represents an integer from 0-4;

Q represents —CN, —C(=NOH)NH$_2$ or —CONHR$^1$; or represents a heterocyclic radical selected from the group consisting of:

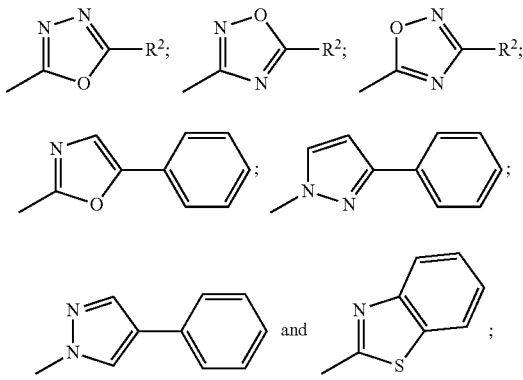

$R^1$ represents hydrogen, aralkyl, aryloxyalkyl, benzocycloalkyl or heteroarylalkyl; and $R^2$ represents amino, aryl, heteroaryl, arylamino, arylalkyl or heteroarylalkyl;

or a pharmaceutically acceptable salt, solvate, ester or prodrug thereof.

Another aspect of the invention is a pharmaceutical composition comprising a therapeutically effective amount of at least one compound of Formula I in a pharmaceutically acceptable carrier.

Yet another aspect of the invention is a method of treating central nervous system diseases such as depression, cognitive diseases and neurodegenerative diseases such as Parkinson's disease, senile dementia or psychoses of organic origin, and stroke, comprising administering a therapeutically acceptable amount of at least one compound of Formula I to a mammal in need of such treatment.

The invention also relates to a method of treating attention related disorders, such as attention deficit disorder (ADD) and attention deficit hyperactivity disorder (ADHD), comprising administering a therapeutically acceptable amount therefor of at least one compound of Formula I to a mammal in need of such treatment.

The invention also relates to a method of treating or preventing Extra-Pyramidal Syndrome (e.g., dystonia, akathisia, pseudoparkinsonism and tardive dyskinesia), of treating primary (idiopathic) dystonia, and of treating or preventing dystonia in patients who exhibit dystonia as a result of treatment with a tricyclic antidepressant, lithium or an anticonvulsant, or who have used cocaine, comprising administering a therapeutically acceptable amount therefor of at least one compound of Formula I to a mammal in need of such treatment.

The invention further relates to a method of treating abnormal movement disorders, such as restless leg syndrome (RLS) or periodic limb movement in sleep (PLMS), comprising administering to a patient in need thereof a therapeutically effective amount therefor of at least one compound of Formula I.

In particular, the invention is drawn to the method of treating Parkinson's disease comprising administering a therapeutically acceptable amount therefor of at least one compound of Formula I to a mammal in need of such treatment.

Still another aspect of the invention is a method of treating Parkinson's disease with a combination of a therapeutically acceptable amount therefor of at least one compound of Formula I and one or more agents useful in the treatment of Parkinson's disease, for example dopamine; a dopaminergic agonist; an inhibitor of monoamine oxidase, type B (MAO-B); a DOPA decarboxylase inhibitor (DCI); or a catechol-O-methyltransferase (COMT) inhibitor.

The invention further relates to a pharmaceutical composition comprising a therapeutically acceptable amount of at least one compound of Formula I and one or more agents known to be useful in the treatment of Parkinson's disease in a pharmaceutically acceptable carrier.

The invention also comprises a method of treating RLS or PLMS comprising administering to a patient in need thereof a therapeutically acceptable amount therefor of a combination of at least one compound of Formula I with another agent useful in treating RLS or PLMS, such as levodopa/carbidopa, levodopa/benserazide, a dopamine agonist, a benzodiazepine, an opioid, an anticonvulsant or iron.

DETAILED DESCRIPTION OF THE INVENTION

In one preferred embodiment, the compound of Formula I or pharmaceutically acceptable salt, solvate, ester or prodrug thereof is one wherein W represents N.

In another preferred embodiment, the compound of Formula I or pharmaceutically acceptable salt, solvate, ester or prodrug thereof is one wherein Q represents —CONHR$^1$.

In another preferred embodiment, the compound of Formula I or pharmaceutically acceptable salt, solvate, ester or prodrug thereof is one wherein 0 represents a heterocyclic radical of the formula:

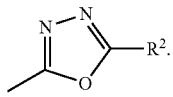

In an especially preferred embodiment, the compound of Formula I or pharmaceutically acceptable salt, solvate, ester or prodrug thereof is one wherein:
  W represents N;
  Z represents hydrogen, halogen or haloalkyl;
  n represents an integer from 0-2;
  Q represents —CONHR$^1$ or represents a heterocyclic radical of the formula:

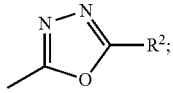

R$^1$ represents aralkyl, benzocycloalkyl or heteroarylalkyl; and
  R$^2$ represents aryl, heteroaryl or arylalkyl.

As used above, and throughout this disclosure, the following terms, unless otherwise indicated, shall be understood to have the following meanings:
  "Patient" includes both human and animals.
  "Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, 2-propynyl, 2-butynyl and 3-methyl-1-butynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination.

Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, haloalkyl, alkylsulfonylalkyl, haloalkoxy, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)— and Y$_1$Y$_2$NSO$_2$—, wherein Y$_1$ and Y$_2$ can be the same or different and are independently selected from the group consisting of hydrogen, alkyl, alkoxycarbonyl, aryl, cycloalkyl, acyl, alkylsulfonyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

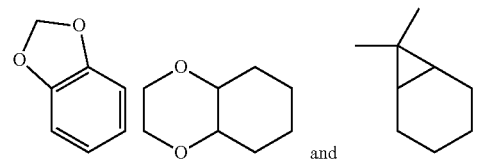

and

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also include a single moiety (e.g., carbonyl) which simultaneously replaces two available hydrogens on the same carbon atom on a ring system. Examples of such moiety are 2-pyrrolidone:

and 3-pyrrolidone:

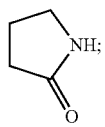

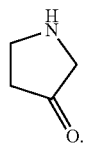

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, 7-oxabicyclo[2.2.1]heptenyl, dihydrothiophenyl, dihydrothiopyranyl, and the like. "Heterocyclenyl" may also include a single moiety (e.g., carbonyl) which simultaneously replaces two available hydrogens on the same carbon atom on a ring system. An example of such moiety is 1,2-dihydro-pyrrol-3-one:

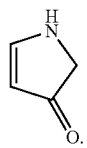

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

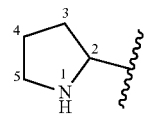

there is no —OH attached directly to carbons marked 2 and 5.

It should also be noted that tautomeric forms such as, for example, the moieties:

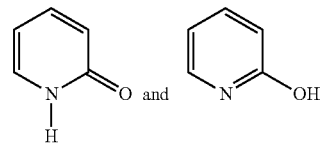 [SMILES: O=c1cccc[nH]1 ; Oc1ccccn1]

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Arylamino" means an aryl-NH— group in which the aryl group is as previously described. Non-limiting example of a suitable arylamino group is phenylamino. The bond to the parent moiety is through the nitrogen.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

The term "pharmaceutical composition" means a composition, as defined above, in a form and comprising active ingredients, vehicles, carriers and/or auxiliaries suitable for pharmaceutical use.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula I or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$) alkyl, and the like.

Similarly, if a compound of Formula I contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula I incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —CH(OH)C(O)O$Y^1$ wherein $Y^1$ is H, ($C_1$-$C_6$)alkyl or benzyl, —CH(O$Y^2$)$Y^3$ wherein $Y^2$ is ($C_1$-$C_4$) alkyl and $Y^3$ is ($C_1$-$C_6$)alkyl, carboxy ($C_1$-$C_6$)alkyl, amino ($C_1$-$C_4$)alkyl or mono-N— or di-N,N—($C_1$-$C_6$)alkylaminoalkyl, —CH($Y^4$)$Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, methyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I, and salts, solvates, esters and prodrugs thereof, may exist in their tautomeric form (for example, as an amide or imino alcohol). All such tautomeric forms are contemplated herein as part of the present invention.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride, separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

In general, the compounds of this invention may be prepared from known or readily prepared starting materials, following methods known to one skilled in the art of organic synthesis. Methods useful for making the amino-quinoxalines and related heterocyclic derivatives are set forth in the Examples below and generalized in Schemes 1-5. Alternative synthetic pathways and analogous structures will be apparent to those skilled in the art or organic synthesis. All stereoisomers and tautomeric forms of the compounds are contemplated.

The preparation of compounds of structure D is illustrated in Scheme 1. Reaction of a carboxylic acid A with thionyl chloride yields quinoxaline B. Quinoxaline B may then be reacted with various amines to give quinoxaline C. Subsequent reaction of quinoxaline C with ammonia at elevated temperature then provides compounds D.

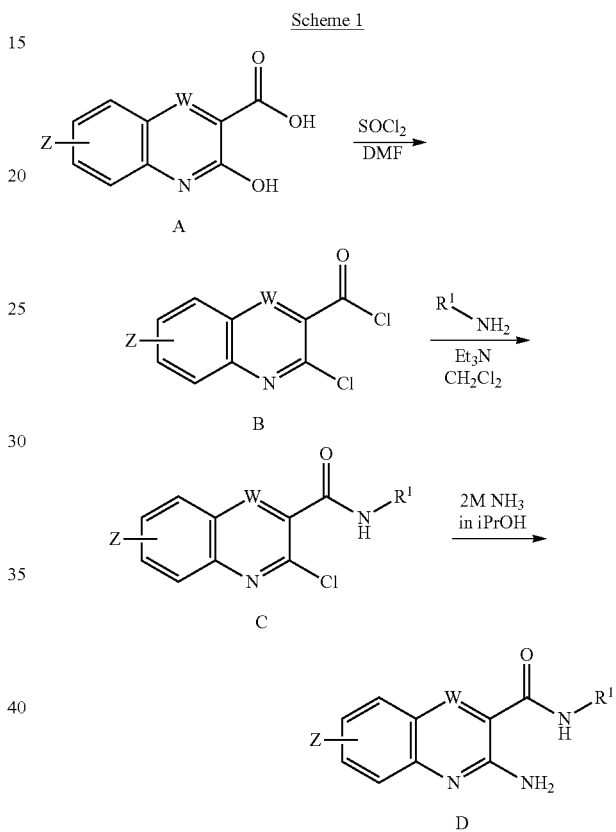

Scheme 1

Compounds of structure H may be prepared as illustrated in Scheme 2. Reaction of a carboxylic acid E with various hydrazides in the presence of EDCI and HOBt in DMSO yields quinoxaline F. Quinoxaline F may then be treated with phosphorus oxychloride to give quinoxaline G. Subsequent reaction of quinoxaline G with ammonia at elevated temperature then provides compounds H.

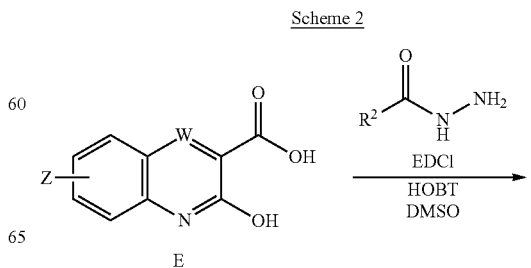

Scheme 2

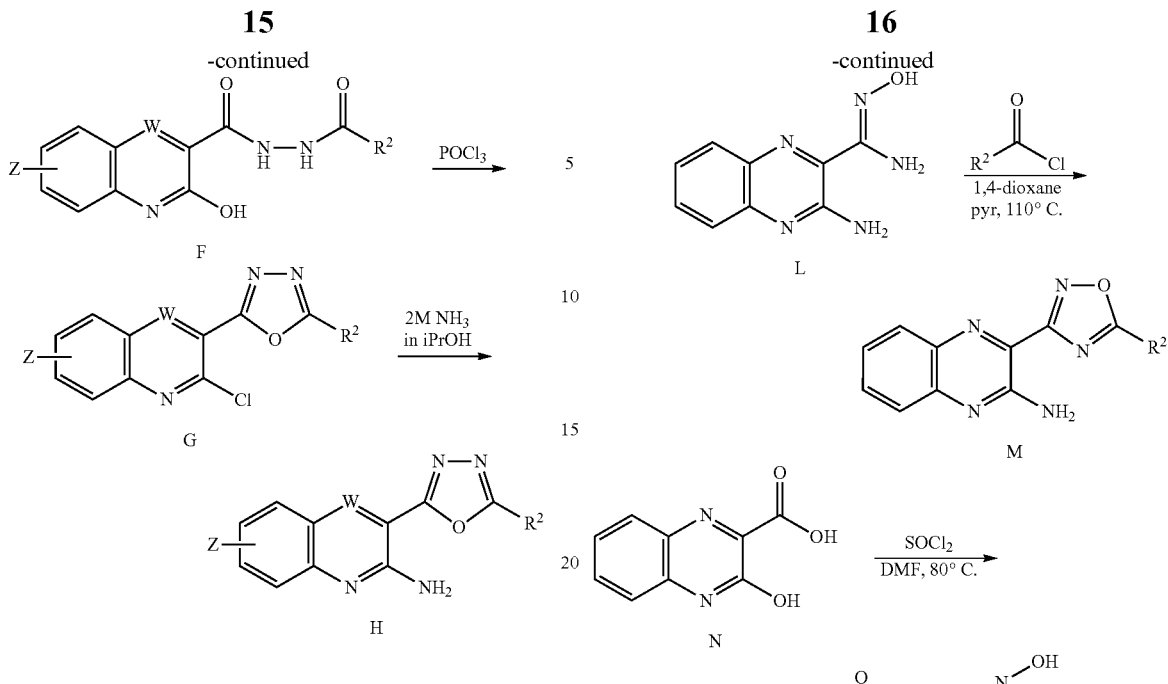

Compounds of structure M may be prepared as illustrated in Scheme 3. Reaction of benzofuroxan I with malononitrile provides 2-amino-3-cyanoquinoxaline 1,4-dioxide J. Reduction of compound J with sodium hydrosulfite yields 2-amino-3-cyanoquinoxaline K. Treatment of quinoxaline K with hydroxylamine hydrochloride provides amide-oxime L. Reaction of compound L with various acid chlorides at high temperature yields compounds of type M.

Compounds of structure R may be prepared as illustrated in Scheme 3. Reaction of quinoxaline carboxylic acid N with thionyl chloride at high temperature provides dichloride O. Treatment of dichloride O with various amide-oximes yields chloride P. Cyclization of compound P is accomplished using POCl$_3$ at high temperature to provide oxadiazole Q. Compounds of type R are produced by reaction of oxadiazole Q with 2M NH$_3$ in isopropanol.

Scheme 3

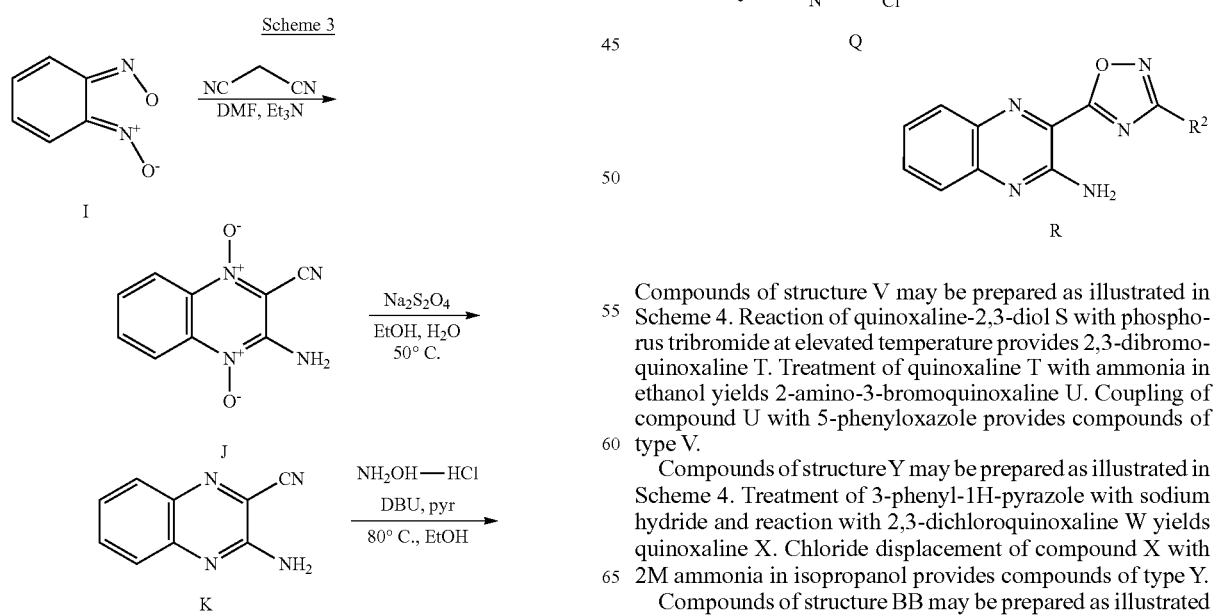

Compounds of structure V may be prepared as illustrated in Scheme 4. Reaction of quinoxaline-2,3-diol S with phosphorus tribromide at elevated temperature provides 2,3-dibromoquinoxaline T. Treatment of quinoxaline T with ammonia in ethanol yields 2-amino-3-bromoquinoxaline U. Coupling of compound U with 5-phenyloxazole provides compounds of type V.

Compounds of structure Y may be prepared as illustrated in Scheme 4. Treatment of 3-phenyl-1H-pyrazole with sodium hydride and reaction with 2,3-dichloroquinoxaline W yields quinoxaline X. Chloride displacement of compound X with 2M ammonia in isopropanol provides compounds of type Y.

Compounds of structure BB may be prepared as illustrated in Scheme 4. Treatment of 2,3-dichloroquinoxaline W with hydrazine hydrate provides hydrazine Z. Condensation of hydrazine Z with 2-phenylmalonaldehyde provides quinoxaline AA. Chloride displacement of compound AA with 2M ammonia in isopropanol provides compounds of type BB.

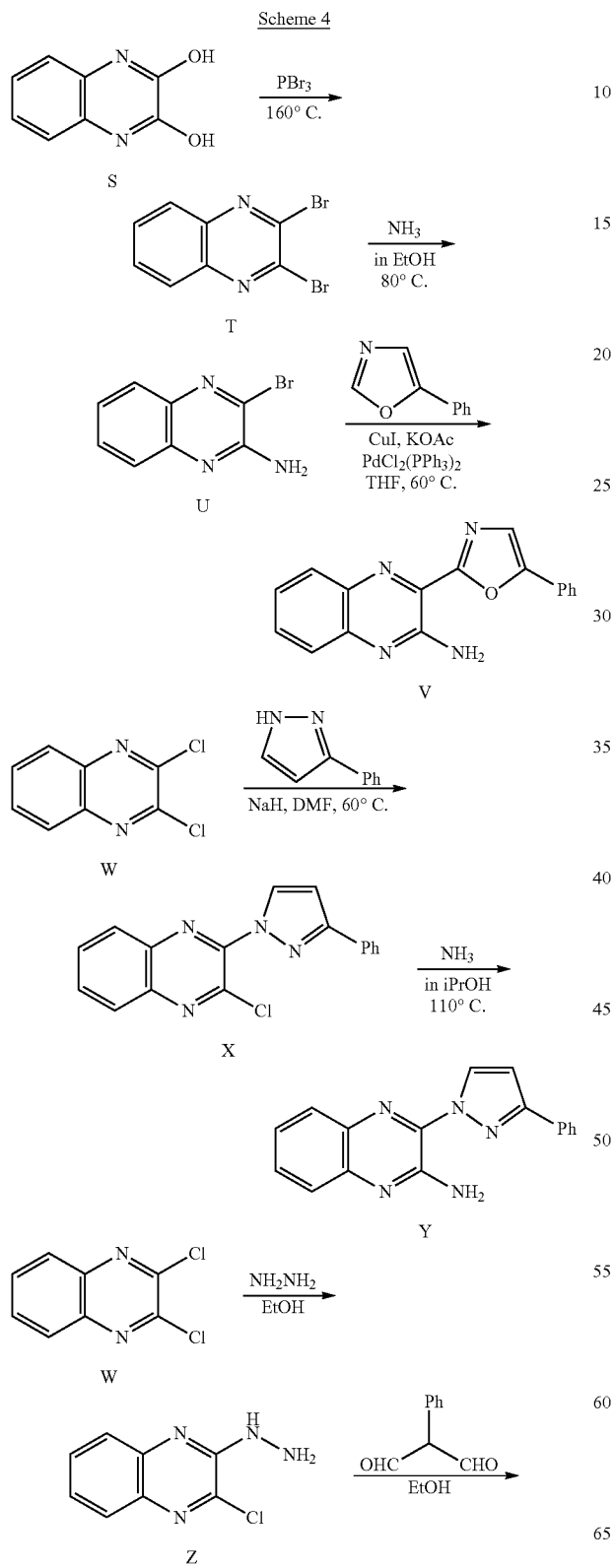

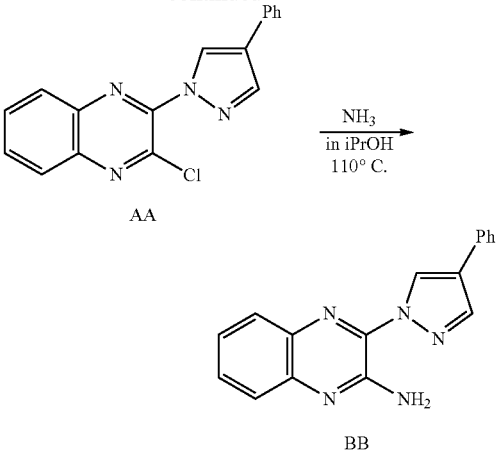

Compounds of structure DD may be prepared as illustrated in Scheme 5. Treatment of benzofuroxan I with 2-(benzo[d]thiazol-2-yl)acetonitrile and sodium tert-butoxide in DMF yields 2-amino-3-(benzo[d]thiazol-2-yl)quinoxaline 1,4-dioxide CC. Reduction of compound CC with sodium hydrosulfite provides compounds of type DD.

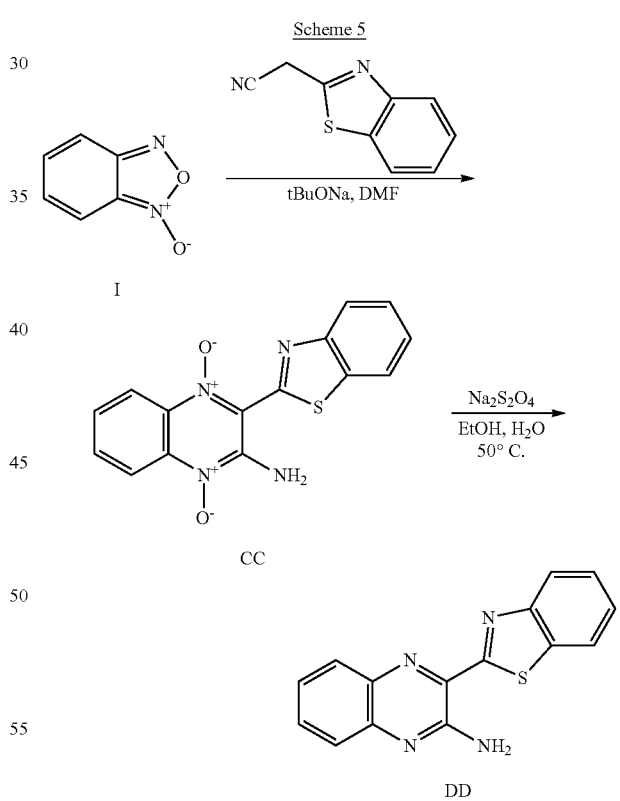

The starting materials and reagents depicted in Schemes 1-5 are either available from commercial suppliers such as Sigma-Aldrich (St. Louis, Mo.) and Acros Organics Co. (Fair Lawn, N.J.), or can be prepared using methods well-known to those of skill in the art of organic synthesis.

One skilled in the art will recognize that the synthesis of compounds of Formula I may require protection of certain functional groups (i.e., derivatization for the purpose of chemical compatibility with a particular reaction condition). Suitable protecting groups for the various functional groups of the compounds of Formula I and methods for their installation and removal may be found in Greene et. al., *Protective Groups in Organic Synthesis*, Wiley-Interscience, New York, (1999).

EXAMPLES

The following examples constitute illustrative examples of compounds of the present invention and are not to be construed as limiting the scope of the disclosure. Alternative mechanistic pathways and analogous structures within the scope of the invention may be apparent to those skilled in the art.

General Methods

Solvents, reagents, and intermediates that are commercially available were used as received. Reagents and intermediates that are not commercially available were prepared in the manner described below. Microwave reactions were performed using the Biotage Initiator microwave. $^1$H NMR spectra were obtained on a Gemini AS-400 (400 MHz) and are reported as ppm down field from Me$_4$Si with number of protons, multiplicities, and coupling constants in Hertz indicated parenthetically. Where LC/MS data are presented, analyses were performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The observed parent ion is given.

The following solvents and reagents may be referred to by their abbreviations:

| | |
|---|---|
| Me = | methyl; |
| Et = | ethyl; |
| Pr = | propyl; |
| Bu = | butyl; |
| Ph = | phenyl, and |
| Ac = | acetyl |
| μl = | microliters |
| EtOAc = | ethyl acetate |
| AcOH or HOAc = | acetic acid |
| Atm = | atmosphere |
| BINAP = | rac-2,2'-bis(diphenylphosphino)-1,1'-binaphthyl |
| Boc or BOC = | tert-butoxycarbonyl |
| BSA = | N,O-(bistrimethylsilyl)acetamide |
| CH$_2$Cl$_2$ = | dichloromethane |
| DIPEA = | diisoproylethylamine |
| DMAP = | 4-dimethylaminopyridine |
| DMF = | dimethylformamide |
| DMSO = | dimethylsulfoxide |
| EDCI = | 1-(3-dimethylaminopropyl)-3-ethylcarbodiimide |
| EDTA = | ethylenediaminetetraacetic acid |
| EtOH = | ethanol |
| g = | grams |
| h = | hour |
| HOBt = | 1-hydroxybenzotriazole |
| LAH = | lithium aluminum hydride |
| LCMS or LC/MS = | liquid chromatography mass spectrometry |
| min = | minute |
| mg = | milligrams |
| mL = | milliliters |
| mmol = | millimoles |
| mCPBA = | 3-chloroperoxybenzoic acid |
| MeOH = | methanol |
| MS = | mass spectrometry |
| NMR = | nuclear magnetic resonance spectrometry |
| RT or rt = | room temperature (ambient, about 25° C.) |
| TEA or Et$_3$N = | triethylamine |
| TFA = | trifluoroacetic acid |
| THF = | tetrahydrofuran |
| TLC = | thin layer chromatography |
| TMS = | trimethylsilyl |
| TMSOTf = | trimethylsilyl trifluoromethanesulfonate |
| TBS = | tert-butyldimethylsilyl |
| X-Phos = | 2-dicyclohexylphosphino-2',4',6'-triisopropylbiphenyl |

In general, the compounds of this invention may be prepared from known or readily prepared starting materials, following methods known to one skilled in the art or organic synthesis. All stereoisomers and tautomeric forms of the compounds are contemplated.

Example 1

Preparation of Compound 1

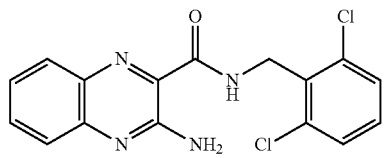

Using Steps B and C described in Example 2, compound 1 was prepared substituting 2,6-dichlorobenzylamine for 2-chloro-6-methylbenzylamine in Step B.

Example 2

Preparation of Compound 2

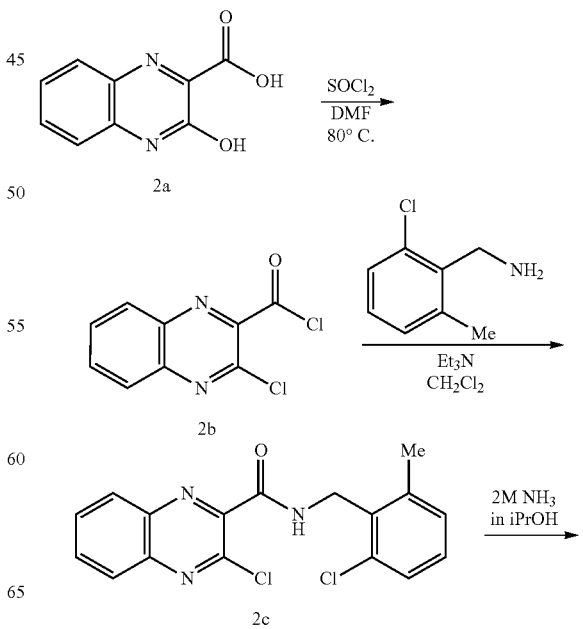

-continued

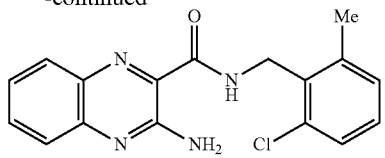

Step A—Synthesis of Compound 2b

To 3-hydroxy-2-quinoxalinecarboxylic acid (1.0 g, 5.3 mmol) was added thionyl chloride (10 mL) and DMF (5 drops) and the solution was stirred and heated to 80° C. for 24 h. Allowed to cool and concentrated under vacuum to give compound 2b (1.2 g, 99%)

Step B—Synthesis of Compound 2c

To compound 2b (100 mg, 0.44 mmol) was added $CH_2Cl_2$ (6 mL), $Et_3N$ (0.09 mL, 0.66 mmol) and 2-chloro-6-methylbenzylamine (78 mg, 0.48 mmol) and the solution was stirred for 1 h. Transferred to sep. funnel, washed with $H_2O$, washed with brine, dried ($MgSO_4$), filtered, and concentrated to give compound 2c (152 mg, 100%).

Step C—Synthesis of Compound 2

To compound 2c (152 mg, 0.44 mmol) was added 2M $NH_3$ in isopropanol (8 mL), (or 2M $NH_3$ in ethanol), the tube sealed and the solution was stirred and heated to 100° C. for 20 h. Allowed to cool and concentrated under vacuum. Crude material was purified by preparative TLC (5% MeOH/$CH_2Cl_2$) to yield compound 2 (140 mg, 98%).

Example 3

Preparation of Compound 3

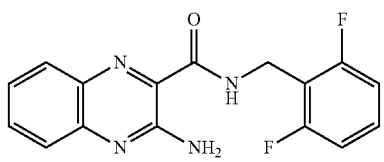

Using Steps B and C described in Example 2, compound 3 was prepared substituting 2,6-difluorobenzylamine for 2-chloro-6-methylbenzylamine in Step B.

Example 4

Preparation of Compound 4

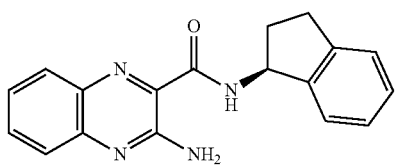

Using Steps B and C described in Example 2, compound 4 was prepared substituting (S)-2,3-dihydro-1H-inden-1-amine for 2-chloro-6-methylbenzylamine in Step B.

Example 5

Preparation of Compound 5

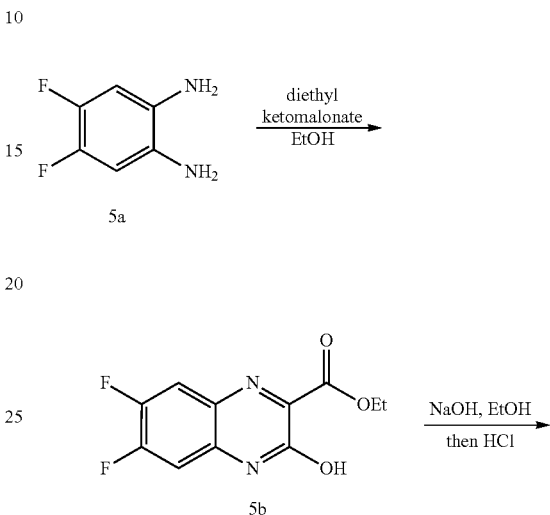

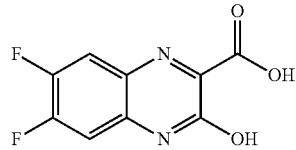

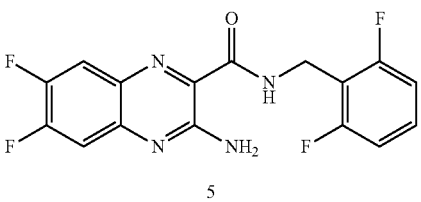

Step A—Synthesis of Compound 5b

To compound 5a (2.2 g, 15.3 mmol) was added EtOH (40 mL), and diethyl ketomalonate (2.83 mL, 18.3 mmol) and the solution was stirred and heated to reflux for 16 h. Allowed to cool and concentrated under vacuum. Purified by flash column chromatography using silica gel (30% EtOAc/hexanes) to yield compound 5b (3.2 g, 82%).

Step B—Synthesis of Compound 5c

To compound 5b (2.0 g, 7.9 mmol) was added 1N NaOH (23.6 mL, 23.6 mmol) and EtOH (20 mL) and the solution was heated to reflux for 2 h. Allowed to cool, added 1N HCl (25 mL) and the solution was stirred for 30 min. Filtered solid and dried to yield compound 5c (1.3 g, 73%).

Step C—Synthesis of Compound 5

Using Steps A, B, and C from Example 2, substituting compound 5c for compound 2a and substituting 2,6-difluorobenzylamine for 2-chloro-6-methylbenzylamine, compound 5 was prepared.

Example 6

Preparation of Compound 6

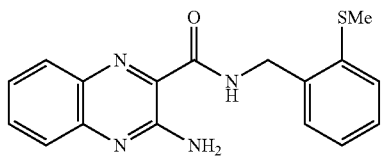

6

Using Steps B and C described in Example 2, compound 6 was prepared substituting 2-methylthiobenzylamine for 2-chloro-6-methylbenzylamine in Step B.

Example 7

Preparation of Compound 7

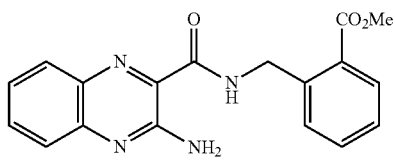

7

Using Steps B and C described in Example 2, compound 7 was prepared substituting methyl 2-(aminomethyl)benzoate for 2-chloro-6-methylbenzylamine in Step B.

Example 8

Preparation of Compound 8

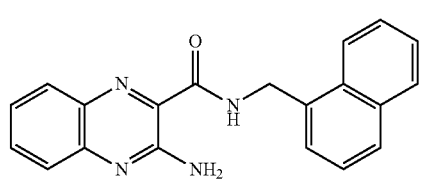

8

Using Steps B and C described in Example 2, compound 8 was prepared substituting 1-naphthalenemethylamine for 2-chloro-6-methylbenzylamine in Step B.

Example 9

Preparation of Compound 9

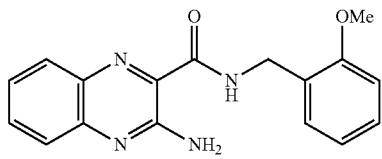

9

Using Steps B and C described in Example 2, compound 9 was prepared substituting 2-methoxybenzylamine for 2-chloro-6-methylbenzylamine in Step B.

Example 10

Preparation of Compound 10

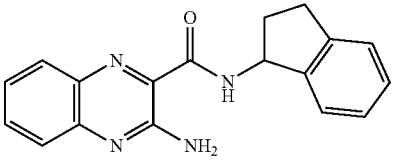

10

Using Steps B and C described in Example 2, compound 10 was prepared substituting 2,3-dihydro-1H-inden-1-amine for 2-chloro-6-methylbenzylamine in Step B.

Example 11

Preparation of Compound 11

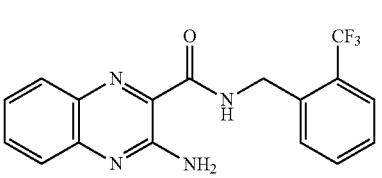

11

Using Steps B and C described in Example 2, compound 11 was prepared substituting 2-trifluoromethylbenzylamine for 2-chloro-6-methylbenzylamine in Step B.

Example 12

Preparation of Compound 12

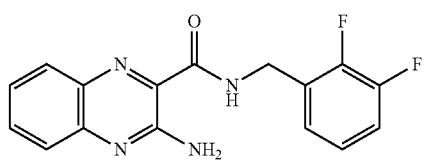

Using Steps B and C described in Example 2, compound 12 was prepared substituting 2,3-difluorobenzylamine for 2-chloro-6-methylbenzylamine in Step B.

Example 13

Preparation of Compounds 13b and 13

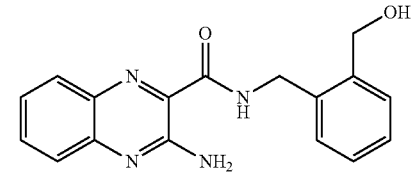

Step A—Synthesis of Compound 13b

To a solution of LiAlH$_4$ (5.6 g, 147 mmol) in ether (45 mL) was added methyl 2-cyanobenzoate (4.8 g, 30 mmol) in ether (75 mL) and the solution was stirred for 5 h at reflux. Cooled solution in an ice bath, added water drop wise, white solid was removed by filtration and rinsed with ether. The ether layer was dried (MgSO$_4$), filtered, concentrated, added 4N HCl in dioxane, filtered salt, and recrystallized from ethyl acetate to give compound 13b as the HCl salt (2.26 g, 43%).

Step B—Synthesis of Compound 13

Using Steps B and C described in Example 2, compound 13 was prepared substituting compound 13b for 2-chloro-6-methylbenzylamine in Step B.

Example 14

Preparation of Compound 14

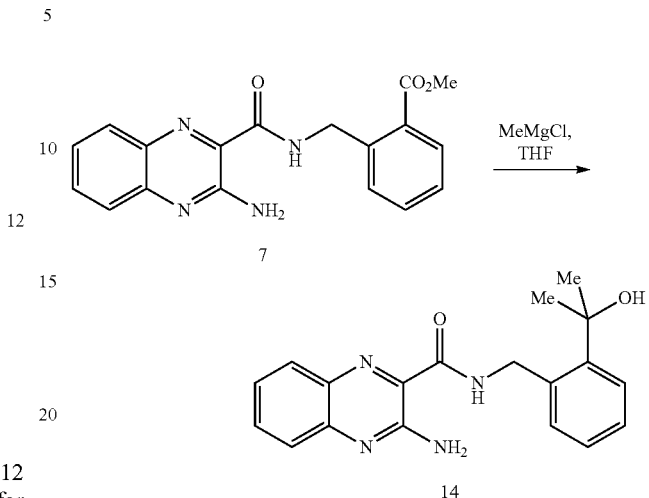

Step A—Synthesis of Compound 14

To compound 7 (57 mg, 0.17 mmol) was added THF (6 mL), and MeMgCl (3.0M in THF, 0.17 mL, 0.51 mmol) and the solution was stirred 5 h. The reaction was concentrated under vacuum and purified by preparative TLC (5% CH$_3$OH/CH$_2$Cl$_2$) to yield compound 14 (8 mg, 14%).

Example 15

Preparation of Compound 15

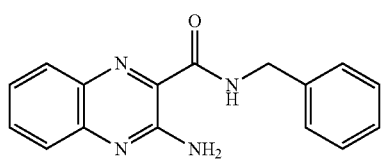

Using Steps B and C described in Example 2, compound 15 was prepared substituting benzylamine for 2-chloro-6-methylbenzylamine in Step B.

Example 16

Preparation of Compound 16

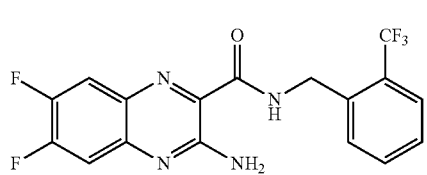

Using Step C described in Example 5, substituting 2-trifluoromethylbenzylamine for 2,6-difluorobenzylamine, compound 16 was prepared.

Example 17

Preparation of Compound 17

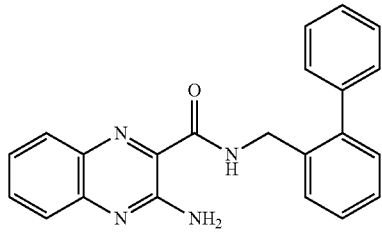

17

Using Steps B and C described in Example 2, compound 17 was prepared substituting 2-phenylbenzylamine for 2-chloro-6-methylbenzylamine in Step B.

Example 18

Preparation of Compound 18

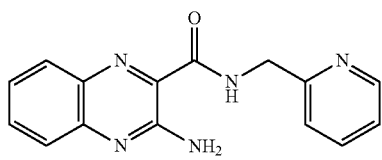

18

Using Steps B and C described in Example 2, compound 18 was prepared substituting 2-aminomethylpyridine for 2-chloro-6-methylbenzylamine in Step B.

Example 19

Preparation of Compounds 19c and 19

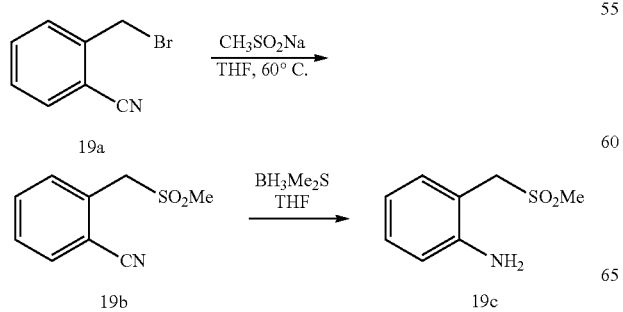

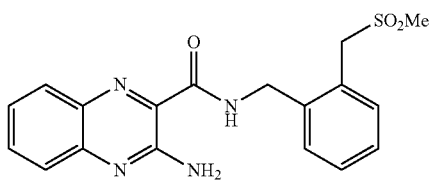

19

Step A—Synthesis of Compound 19b

To compound 19a (3.0 g, 15.3 mmol) was added THF (25 mL), and methanesulfinic acid sodium salt (1.77 g, 16.8 mmol) and the solution was stirred and heated to reflux for 31 h. Removed solid precipitate and concentrated filtrate to yield compound 19b (2.73 g, 91%).

Step B—Synthesis of Compound 19c

To compound 19b (200 mg, 1.02 mmol) was added THF (6 mL), cooled in an ice bath, and added $BH_3.Me_2S$ complex (2M in THF, 3.1 mL, 3.06 mmol). The solution was stirred at 0° C. for 30 min and room temperature for 17 h. To the solution was added MeOH, concentrated under vacuum, and purified by flash column chromatography to yield compound 19c (128 mg, 62%).

Step C—Synthesis of Compound 19

Using Steps B and C described in Example 2, compound 19 was prepared substituting compound 19c for 2-chloro-6-methylbenzylamine in Step B.

Example 20

Preparation of Compound 20

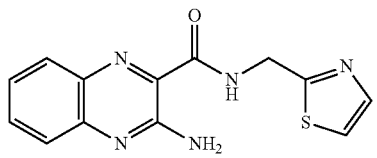

20

Using Steps B and C described in Example 2, compound 20 was prepared substituting 2-aminomethylthiazole for 2-chloro-6-methylbenzylamine in Step B.

Example 21

Preparation of Compound 21

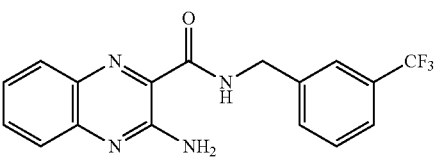

21

Using Steps B and C described in Example 2, compound 21 was prepared substituting 3-trifluoromethylbenzylamine for 2-chloro-6-methylbenzylamine in Step B.

Example 22

Preparation of Compound 22

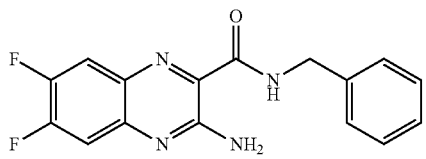

Using Step C described in Example 5, substituting benzylamine for 2,6-difluorobenzylamine, compound 22 was prepared.

Example 23

Preparation of Compound 23

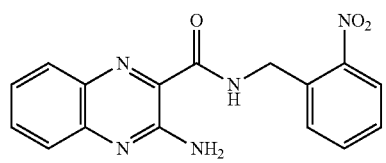

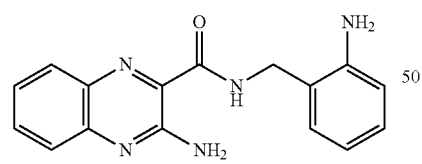

Step A—Synthesis of Compound 23

To compound 24 (225 mg, 0.70 mmol) was added EtOH (8 mL), $H_2O$ (2 mL), AcOH (10 mL), Fe powder (292 mg, 5.2 mmol), and conc. HCl (5 drops) and the solution was stirred for 30 min at 100° C. Allowed to cool, filtered through a plug of celite, and concentrated under vacuum. Purified by preparative TLC (10% MeOH/$CH_2Cl_2$) to give compound 23 (39 mg, 19%).

Example 24

Preparation of Compound 24

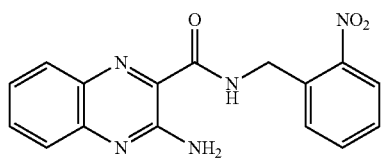

Using Steps B and C described in Example 2, compound 24 was prepared substituting 2-nitrobenzylamine for 2-chloro-6-methylbenzylamine in Step B.

Example 25

Preparation of Compound 25

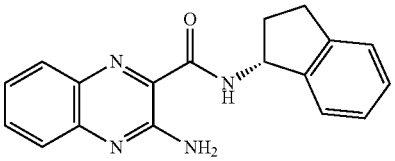

Using Steps B and C described in Example 2, compound 25 was prepared substituting (R)-2,3-dihydro-1H-inden-1-amine for 2-chloro-6-methylbenzylamine in Step B.

Example 26

Preparation of Compound 26

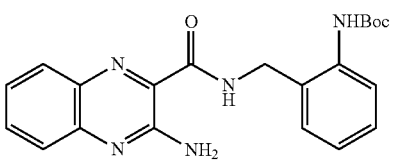

Using Steps B and C described in Example 2, compound 26 was prepared substituting tert-butyl 2-(aminomethyl)phenylcarbamate for 2-chloro-6-methylbenzylamine in Step B.

Example 27

Preparation of Compound 27

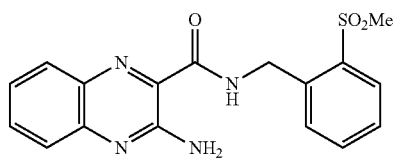
27

Using Steps B and C described in Example 2, compound 27 was prepared substituting 2-(methanesulfonyl)benzylamine hydrochloride for 2-chloro-6-methylbenzylamine in Step B.

Example 28

Preparation of Compound 28

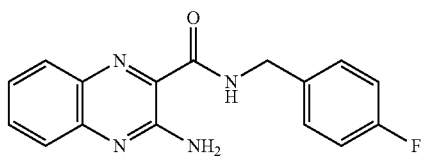
28

Using Steps B and C described in Example 2, compound 28 was prepared substituting 4-fluorobenzylamine for 2-chloro-6-methylbenzylamine in Step B.

Example 29

Preparation of Compound 29

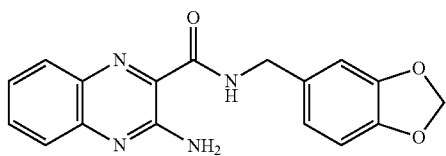 [SMILES: Nc1nc2ccccc2nc1C(=O)NCc1ccc2c(c1)OCO2]
29

Using Steps B and C described in Example 2, compound 29 was prepared substituting 3,4-methylenedioxybenzylamine for 2-chloro-6-methylbenzylamine in Step B.

Example 30

Preparation of Compound 30

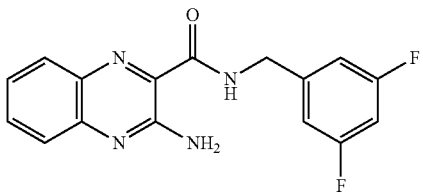
30

Using Steps B and C described in Example 2, compound 30 was prepared substituting 3,5-difluorobenzylamine for 2-chloro-6-methylbenzylamine in Step B.

Example 31

Preparation of Compound 31

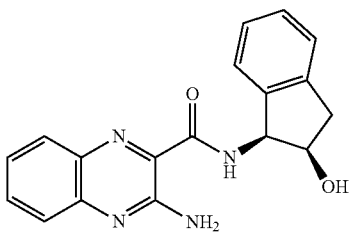
31

Using Steps B and C described in Example 2, compound 31 was prepared substituting (1S,2R)-(−)-cis-1-amino-2-indanol for 2-chloro-6-methylbenzylamine in Step B.

Example 32

Preparation of Compound 32

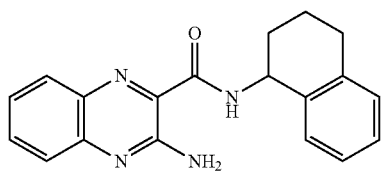
32

Using Steps B and C described in Example 2, compound 32 was prepared substituting 1,2,3,4-tetrahydro-1-naphthylamine for 2-chloro-6-methylbenzylamine in Step B.

Example 33

Preparation of Compound 33

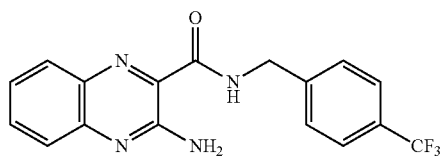

33

Using Steps B and C described in Example 2, compound 33 was prepared substituting 4-trifluoromethylbenzylamine for 2-chloro-6-methylbenzylamine in Step B.

Example 34

Preparation of Compound 34

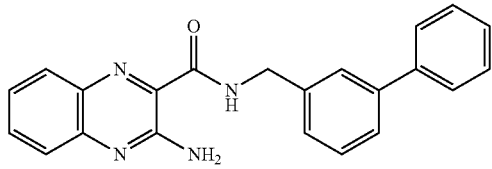

34

Using Steps B and C described in Example 2, compound 34 was prepared substituting 3-phenylbenzylamine for 2-chloro-6-methylbenzylamine in Step B.

Example 35

Preparation of Compound 35

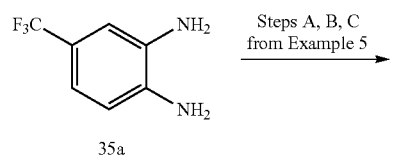

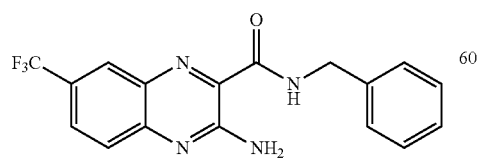

35

Using Steps A, B, and C from Example 5, substituting compound 35a for 5a and substituting benzylamine for 2-chloro-6-methylbenzylamine, compound 35 was prepared.

Example 36

Preparation of Compound 36

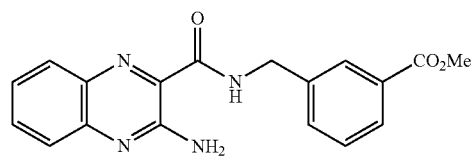

36

Using Steps B and C described in Example 2, compound 36 was prepared substituting methyl 3-(aminomethyl)benzoate for 2-chloro-6-methylbenzylamine in Step B.

Example 37

Preparation of Compound 37

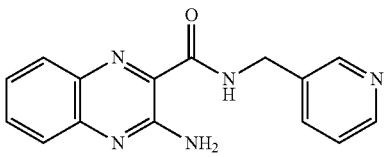

37

Using Steps B and C described in Example 2, compound 37 was prepared substituting 3-aminomethylpyridine for 2-chloro-6-methylbenzylamine in Step B.

Example 38

Preparation of Compound 38

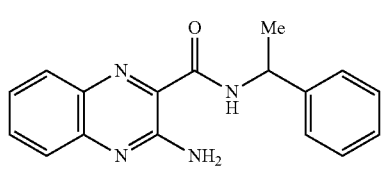

38

Using Steps B and C described in Example 2, compound 38 was prepared substituting DL-a-methylbenzylamine for 2-chloro-6-methylbenzylamine in Step B.

Example 39

Preparation of Compound 39

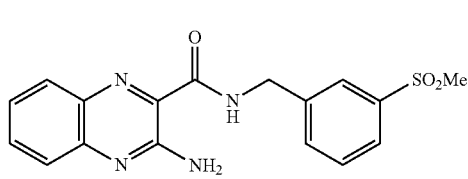

Using Steps B and C described in Example 2, compound 39 was prepared substituting 3-(methanesulfonyl)benzylamine for 2-chloro-6-methylbenzylamine in Step B.

Example 40

Preparation of Compound 40

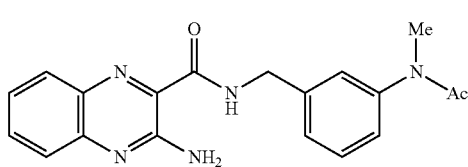

Using Steps B and C described in Example 2, compound 40 was prepared substituting N-[3-(aminomethyl)phenyl]-N-methylacetamide hydrochloride for 2-chloro-6-methylbenzylamine in Step B.

Example 41

Preparation of Compound 41

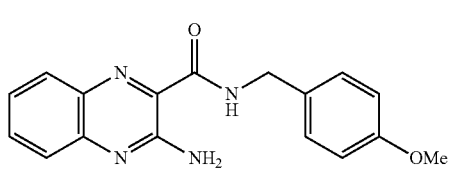

Using Steps B and C described in Example 2, compound 41 was prepared substituting 4-methoxybenzylamine for 2-chloro-6-methylbenzylamine in Step B.

Example 42

Preparation of Compound 42

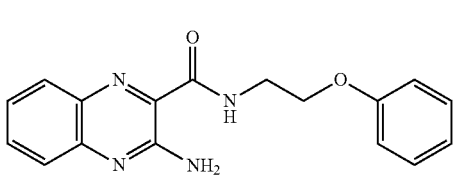

Using Steps B and C described in Example 2, compound 42 was prepared substituting 2-phenoxyethanamine for 2-chloro-6-methylbenzylamine in Step B.

Example 43

Preparation of Compound 43

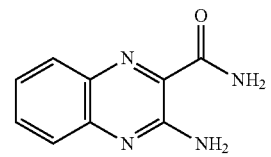

Using Step C described in Example 2, compound 43 was prepared substituting compound 2b for compound 2c.

Example 44

Preparation of Compound 44

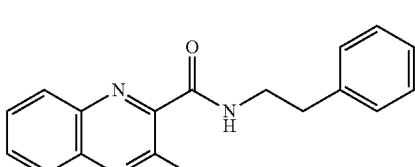

Using Steps B and C described in Example 2, compound 44 was prepared substituting 2-phenethylamine for 2-chloro-6-methylbenzylamine in Step B.

Example 45

Preparation of Compound 45

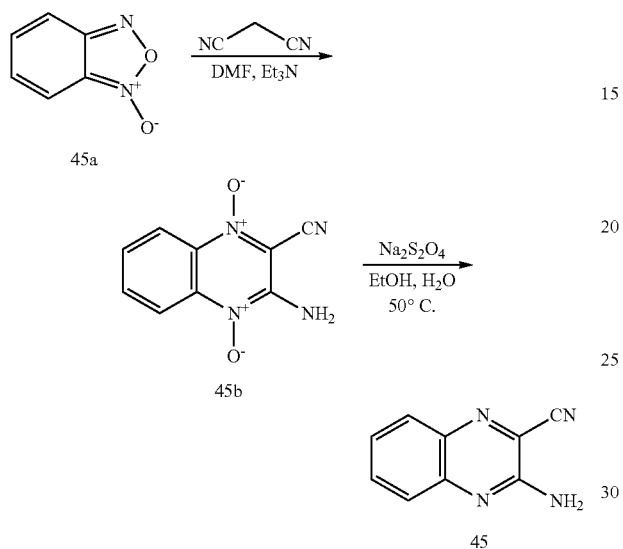

Step A—Synthesis of Compound 45b

To benzofuroxan (20 g, 147 mmol) was added DMF (100 mL), Et$_3$N (3.0 mL, 21.5 mmol), and malononitrile (10 g, 156 mmol) and the solution was stirred at 0° C. for 3 h. The solution was filtered, rinsed with ether, and dried to yield compound 45b (23 g, 77%).

Step B—Synthesis of Compound 45

To compound 45b (2.0 g, 9.9 mmol) was added MeOH (20 mL) and the solution was heated to 50° C. A solution of Na$_2$S$_2$O$_4$ (4.8 g, 28 mmol) in H$_2$O (20 mL) was added and the solution was stirred for 6 h. To the solution was added a solution of Na$_2$S$_2$O$_4$ (4.8 g, 28 mmol) in H$_2$O (20 mL) and the solution was stirred for 12 h. Allowed to cool to room temperature, filtered yellow solid and dried to yield compound 45 (1.3 g, 78%).

Example 46

Preparation of Compound 46

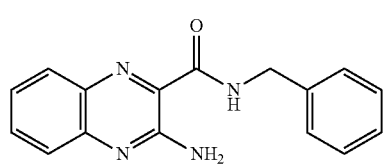

Using Steps A, B, and C described in Example 2, compound 46 was prepared substituting 2-chloro-3-quinolinecarboxylic acid for compound 2a in Step A and substituting benzylamine for 2-chloro-6-methylbenzylamine in Step B.

Example 47

Preparation of Comound 47

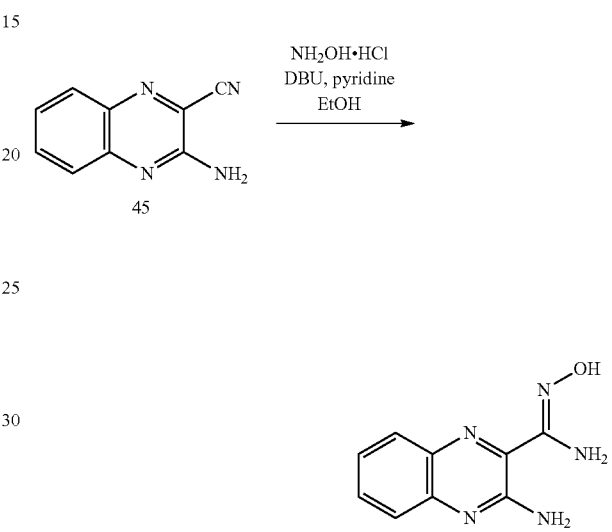

Step A—Synthesis of Compound 47

To compound 45 (1.0 g, 5.9 mmol) were added EtOH (30 mL), pyridine (5 mL, 62 mmol), DBU (0.1 mL, 0.7 mmol), and hydroxylamine hydrochloride (0.8 g, 12 mmol). The solution was heated to reflux for 5 h. Allowed to cool and sit for 16 h. Solid was collected by filtration to yield compound 47 (1.1 g, 92%).

Example 48

Preparation of Compound 48

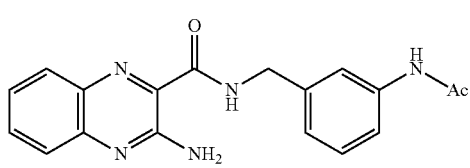

Using Steps B and C described in Example 2, compound 48 was prepared substituting N-[3-(aminomethyl)phenyl]acetamide hydrochloride for 2-chloro-6-methylbenzylamine in Step B.

Example 49

Preparation of Compound 49

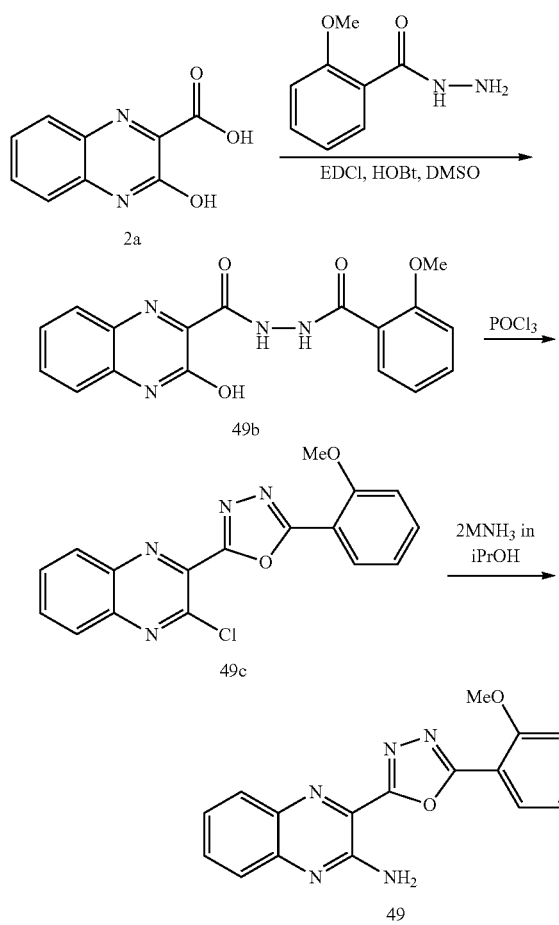

Step A—Synthesis of Compound 49b

To compound 2a (150 mg, 0.79 mmol) was added 2-methoxybenzohydrazide (171 mg, 1.0 mmol), EDCI (228 mg, 1.19 mmol), HOBt (161 mg, 1.19 mmol), and DMSO (6 mL) and the solution was stirred for 16 h. To the solution was added $H_2O$ (150 mL), stirred for 20 min, filtered solid, and dried to yield compound 49b (255 mg, 95%).

Step B—Synthesis of Compound 49c

To compound 49b (255 mg, 0.77 mmol) was added $POCl_3$ (20 mL) and the solution was stirred and heated to 105° C. for 16 h. Allowed to cool, concentrated under vacuum, added $H_2O$ (100 mL), stirred for 30 min, filtered solid and dried to yield compound 49c (245 mg, 96%).

Step C—Synthesis of Compound 49

To compound 49c (245 mg, 0.72 mmol) was added 2M $NH_3$ in isopropanol (15 mL), the tube sealed, stirred, and heated to 80° C. for 24 h. Allowed to cool, filtered solid, rinsed with MeOH, and dried to yield compound 49 (190 mg, 83%).

Example 50

Preparation of Compound 50

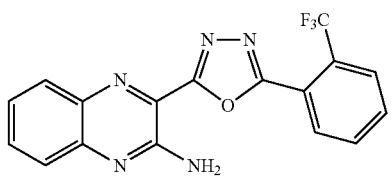

Using Steps A, B, and C from Example 49, substituting 2-trifluoromethylbenzohydrazide for 2-methoxybenzohydrazide, compound 50 was prepared.

Example 51

Preparation of Compound 51

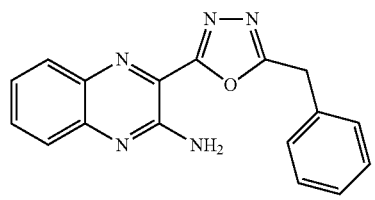

Using Steps A, B, and C from Example 49, substituting 2-phenylacetohydrazide for 2-methoxybenzohydrazide, compound 51 was prepared.

Example 52

Preparation of Compounds 52b and 52

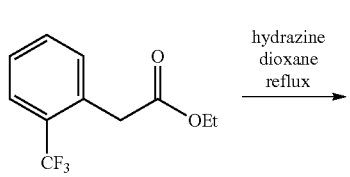

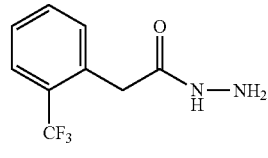

-continued

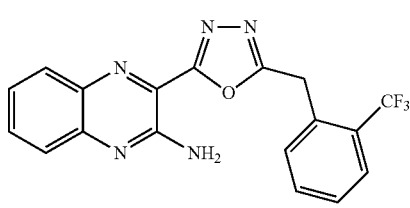
52

Step A—Synthesis of Compound 52b

To compound 52a (1.0 g, 4.3 mmol) was added 1,4-dioxane (10 mL), and hydrazine (1.35 mL, 43 mmol), and the solution was stirred at reflux for 16 h. Allowed to cool and concentrated under vacuum to yield compound 52b (0.94 g, 100%).

Step B—Synthesis of Compound 52

Using Steps A, B, and C from Example 49, substituting compound 52b for 2-methoxybenzohydrazide, compound 52 was prepared.

Example 53

Preparation of Compounds 53a and 53

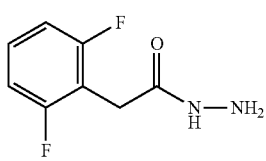
53a

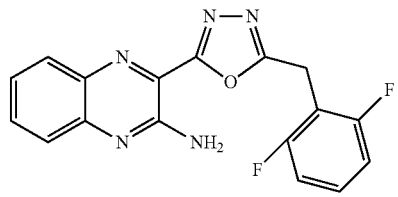
53

Using Steps A, B, and C from Example 49, substituting compound 53a (prepared using Step A from Example 52 substituting ethyl 2-(2,6-difluorophenyl)acetate for compound 52a) for 2-methoxybenzohydrazide, compound 53 was prepared.

Example 54

Preparation of Compound 54

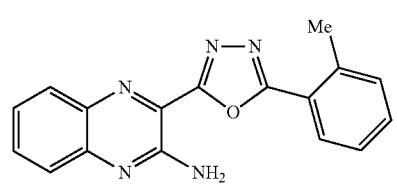
54

Using Steps A, B, and C from Example 49, substituting 2-methylbenzohydrazide for 2-methoxybenzohydrazide, compound 54 was prepared.

Example 55

Preparation of Compounds 55a and 55

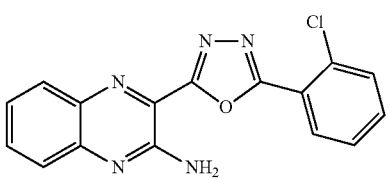
55a

55

Using Steps A, B, and C from Example 49, substituting compound 55a (prepared using Step A from Example 52 substituting ethyl 2-(trifluoromethoxy)benzoate for compound 52a) for 2-methoxybenzohydrazide, compound 55 was prepared.

Example 56

Preparation of Compound 56

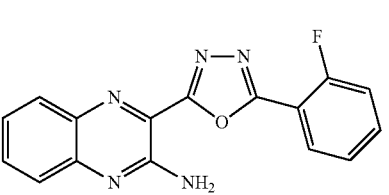
56

Using Steps A, B, and C from Example 49, substituting 2-chlorobenzohydrazide for 2-methoxybenzohydrazide, compound 56 was prepared.

Example 57

Preparation of Compound 57

57

Using Steps A, B, and C from Example 49, substituting 2-fluorobenzohydrazide for 2-methoxybenzohydrazide, compound 57 was prepared.

Example 58

Preparation of Compound 58

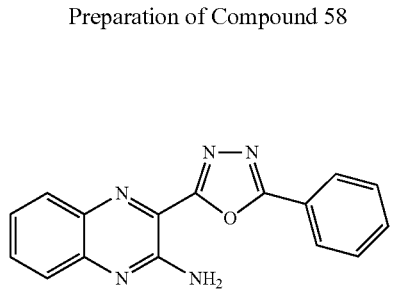
58

Using Steps A, B, and C from Example 49, substituting benzohydrazide for 2-methoxybenzohydrazide, compound 58 was prepared.

Example 59

Preparation of Compound 59

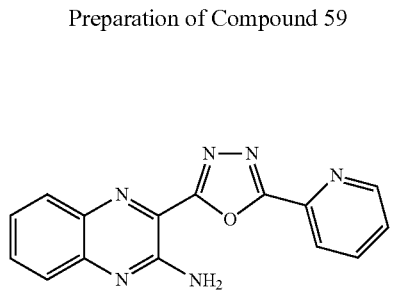
59

Using Steps A, B, and C from Example 49, substituting 2-picolinohydrazide for 2-methoxybenzohydrazide, compound 59 was prepared.

Example 60

Preparation of Compound 60

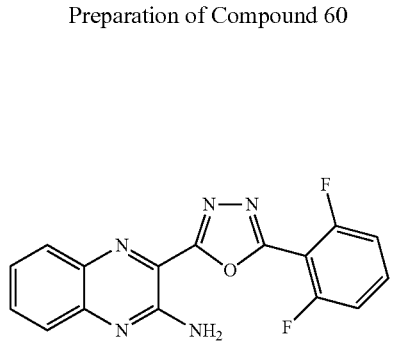
60

Using Steps A, B, and C from Example 49, substituting 2,6-difluorobenzohydrazide for 2-methoxybenzohydrazide, compound 60 was prepared.

Example 61

Preparation of Compound 61

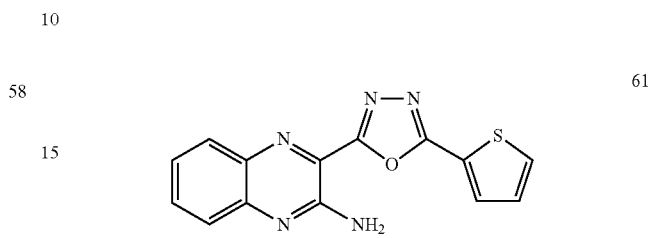
61

Using Steps A, B, and C from Example 49, substituting thiophene-2-carbohydrazide for 2-methoxybenzohydrazide, compound 61 was prepared.

Example 62

Preparation of Compounds 62 and 86

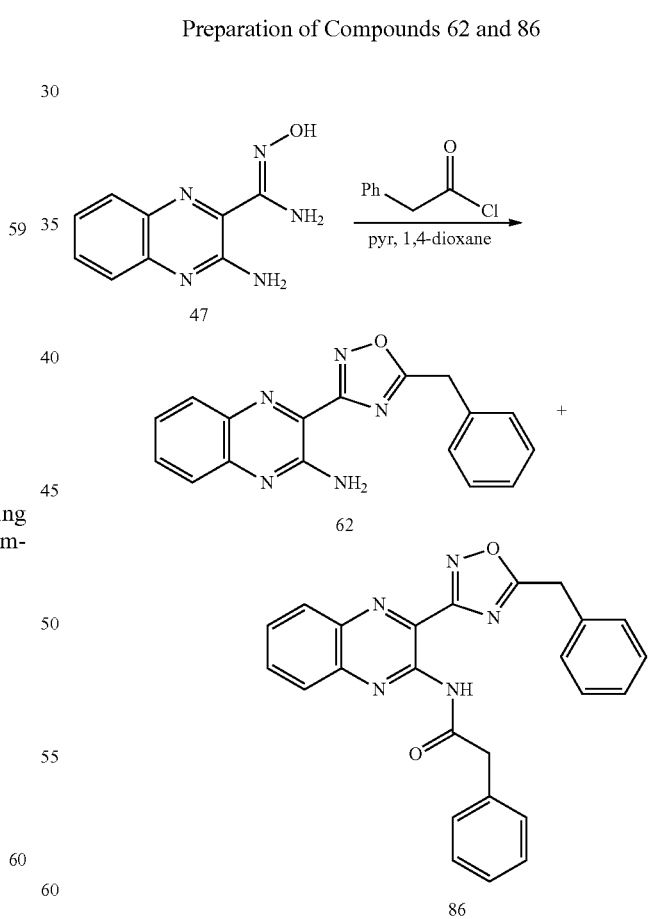

Step A—Synthesis of Compound 62 and 86

To compound 47 (300 mg, 1.48 mmol) was added 1,4-dioxane (10 mL), pyridine (1.0 mL, 12.5 mmol), and phenylacetyl chloride (0.236 mL, 1.78 mmol). The solution was stirred for 16 h. Purified reaction by preparative TLC (30% EtOAc/hexanes) to yield compound 62 (50 mg, 11%) and compound 86 (13 mg, 3%).

Example 63

Preparation of Compound 63

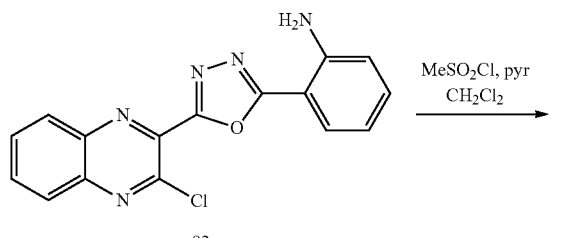

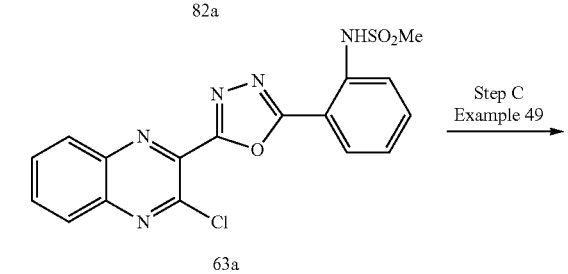

Step A—Synthesis of Compound 63a

To compound 82a (prepared in Example 82, 150 mg, 0.39 mmol) were added CH$_2$Cl$_2$ (10 mL), pyridine (0.065 mL, 0.79 mmol), and methanesulfonylchloride (0.061 mL, 0.79 mmol) and the solution was stirred for 14 h. Purified the reaction by preparative TLC (25% EtOAc/hexanes) to yield compound 63a (130 mg, 83%).

Step B—Synthesis of Compound 63

Using Step C from Example 49, substituting compound 63a for compound 49c, compound 63 was prepared.

Example 64

Preparation of Compound 64

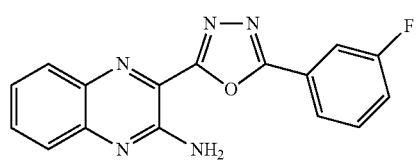

Using Steps A, B, and C from Example 49, substituting 2-fluorobenzohydrazide for 2-methoxybenzohydrazide, compound 64 was prepared.

Example 65

Preparation of Compound 65

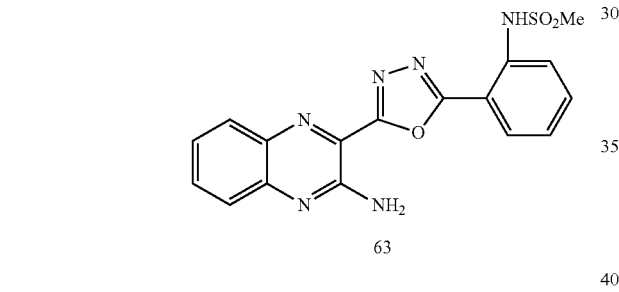

Using Steps A, B, and C from Example 49, substituting 2-(methylsulfonyl)benzohydrazide for 2-methoxybenzohydrazide, compound 65 was prepared.

Example 66

Preparation of Compound 66

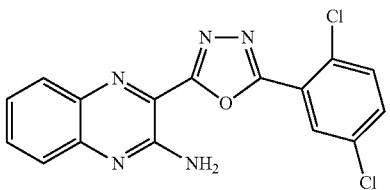

Using Steps A, B, and C from Example 49, substituting 2,5-dichlorobenzohydrazide for 2-methoxybenzohydrazide, compound 66 was prepared.

Example 67

Preparation of Compound 67

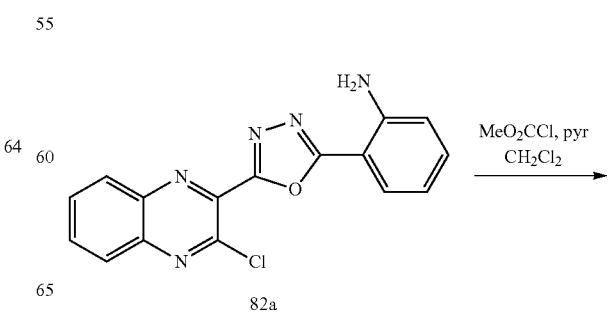

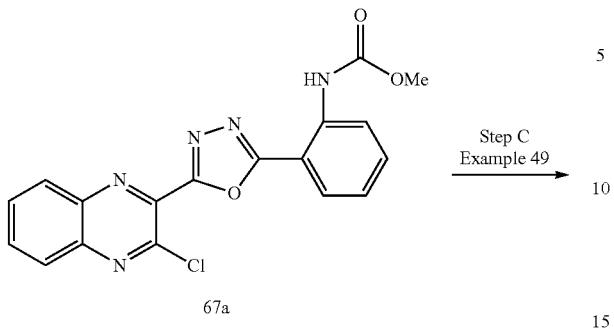

67a

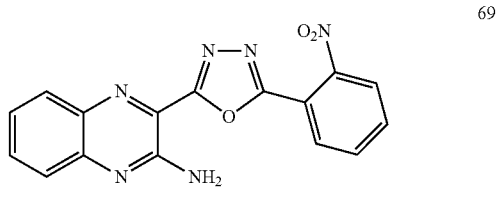 [SMILES: Nc1nc2ccccc2nc1-c1nnc(-c2ccccc2[N+](=O)[O-])o1]

69

Example 69

Preparation of Compound 69

Using Steps A, B, and C from Example 49, substituting 2-nitrobenzohydrazide for 2-methoxybenzohydrazide, compound 69 was prepared.

Example 70

Preparation of Compound 70

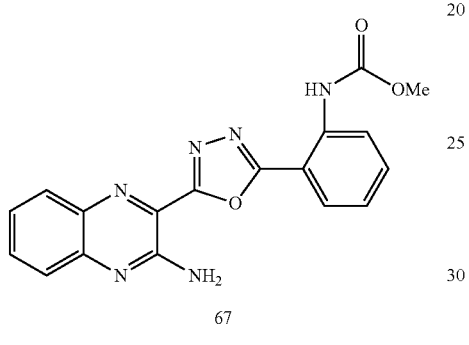

67

Step A—Synthesis of Compound 67a

To compound 82a (prepared in Example 82, 200 mg, 0.62 mmol) were added $CH_2Cl_2$ (6 mL), pyridine (0.10 mL, 1.24 mmol), and methyl chloroformate (0.062 mL, 0.79 mmol) and the solution was stirred for 1 h. Transferred solution to sep. funnel, added $H_2O$ (50 mL), added $CH_2Cl_2$ (50 mL), mixed, separated, dried ($MgSO_4$), filtered, and concentrated to yield compound 67a.

Step B—Synthesis of Compound 67

Using Step C from Example 49, substituting compound 67a for compound 49c, compound 67 was prepared.

Example 68

Preparation of Compound 68

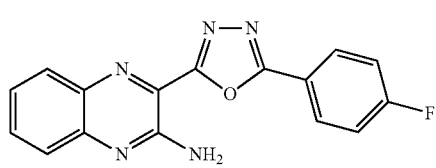

68

Using Steps A, B, and C from Example 49, substituting 4-fluorobenzohydrazide for 2-methoxybenzohydrazide, compound 68 was prepared.

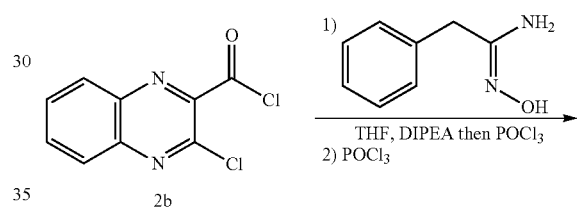

2b

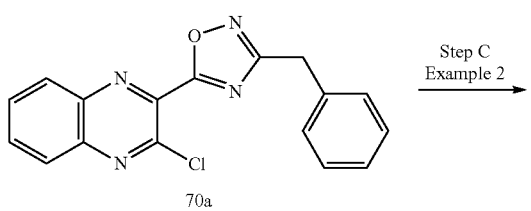

70a

70

Step A—Synthesis of Compound 70a

To compound 2b (477 mg, 2.10 mmol) were added THF (20 mL), DIPEA (0.55 mL, 3.15 mmol), N'-hydroxy-2-phenylacetimidamide (316 mg, 2.10 mmol) and the solution was stirred for 16 h. Reaction was concentrated and $POCl_3$ (10 mL) was added and the solution was stirred and heated to 100° C. for 16 h. Allowed to cool, concentrated under vacuum, added ice water, extracted with $CH_2Cl_2$, dried ($MgSO_4$), filtered and concentrated. Purified by preparative TLC (30% EtOAc/hexanes) to yield compound 70a (200 mg, 30%).

Step B—Synthesis of Compound 70

Using Step C from Example 2, substituting compound 70a for compound 2c, compound 70 was prepared.

Example 71

Preparation of Compound 71

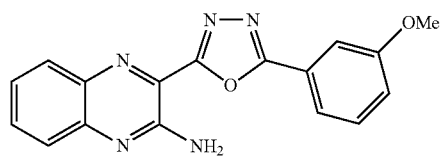

Using Steps A, B, and C from Example 49, substituting 3-methoxybenzohydrazide for 2-methoxybenzohydrazide, compound 71 was prepared.

Example 72

Preparation of Compound 72

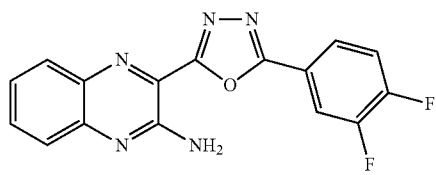

Using Steps A, B, and C from Example 49, substituting 3,4-difluorobenzohydrazide for 2-methoxybenzohydrazide, compound 72 was prepared.

Example 73

Preparation of Compound 73

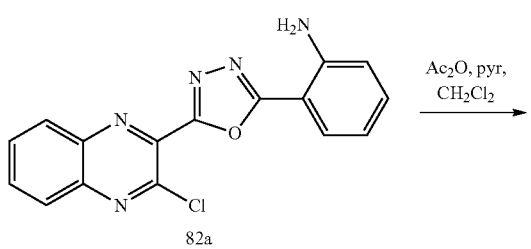

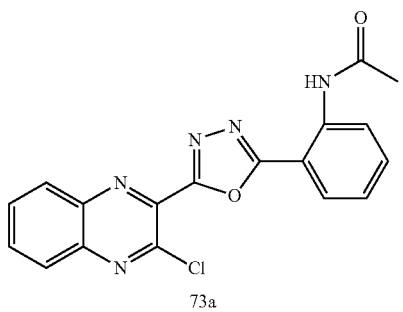

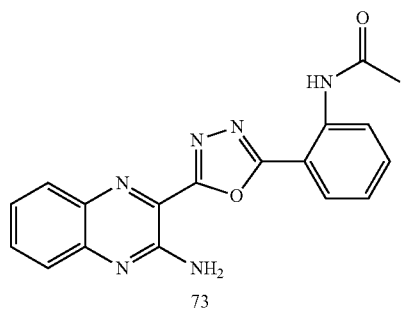

Step A—Synthesis of Compound 73a To compound 82a (prepared in Example 82, 150 mg, 0.39 mmol) were added $CH_2Cl_2$ (8 mL), pyridine (0.065 mL, 0.79 mmol), and acetic anhydride (0.07 mL, 0.79 mmol) and the solution was stirred for 16 h. Purified the reaction by preparative TLC (30% EtOAc/hexanes) to yield compound 73a (140 mg, 98%).

Step B—Synthesis of Compound 73

Using Step C from Example 49, substituting compound 73a for compound 49c, compound 73 was prepared.

Example 74

Preparation of Compound 74

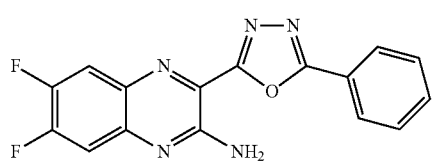

Using Steps A, B, and C from Example 49, substituting compound 5c for compound 2a and substituting benzohydrazide for 2-methoxybenzohydrazide, compound 74 was prepared.

Example 75

Preparation of Compound 75

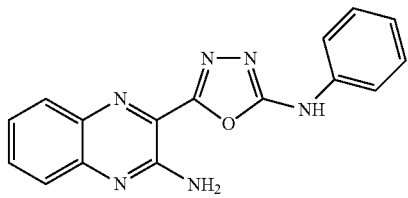
75

Using Steps A, B, and C from Example 49, substituting N-phenylhydrazinecarboxamide for 2-methoxybenzohydrazide, compound 75 was prepared.

Example 76

Preparation of Compound 76

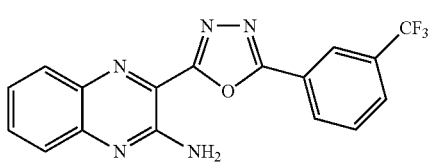
76

Using Steps A, B, and C from Example 49, substituting 3-trifluoromethylbenzohydrazide for 2-methoxybenzohydrazide, compound 76 was prepared.

Example 77

Preparation of Compound 77

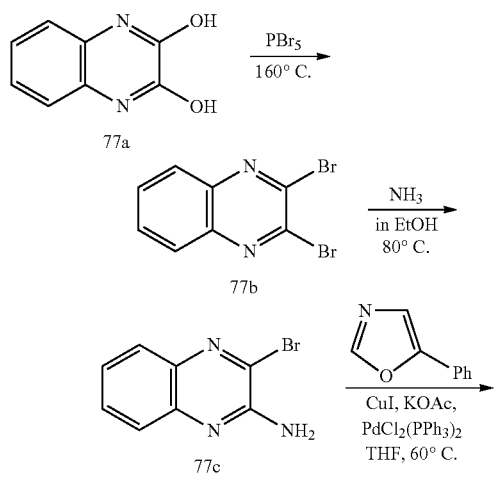

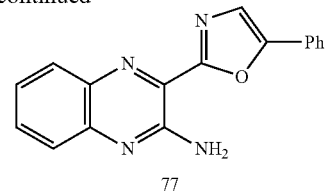
77

Step A—Synthesis of Compound 77b

To compound 77a (3.0 g, 18.5 mmol) were added PBr$_5$ (17 g) and the solution was heated to 160° C. for 2 h. Cooled to 0° C. and added ice and stirred for 30 min. The solution was extracted with CH$_2$Cl$_2$, washed with 1N NaOH, dried (MgSO$_4$), filtered, and concentrated to give compound 77b (5.2 g, 98%).

Step B—Synthesis of Compound 77c

Using Step C from Example 2, substituting compound 77b for compound 2c, compound 77c was prepared.

Step C—Synthesis of Compound 77

To compound 77c (150 mg, 0.67 mmol) was added KOAc (131 mg, 1.3 mmol), CuI (19 mg, 0.066 mmol), PdCl$_2$(PPh$_3$)$_2$ (35 mg, 0.066 mmol), THF (3 mL), and 5-phenyloxazole (97 mg, 0.67 mmol). The solution was stirred and heated to 60° C. for 48 h. The reaction was purified by preparative TLC (30% EtOAc/hexanes) to yield compound 77 (20 mg, 10%).

Example 78

Preparation of Compound 78

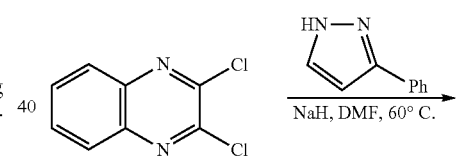

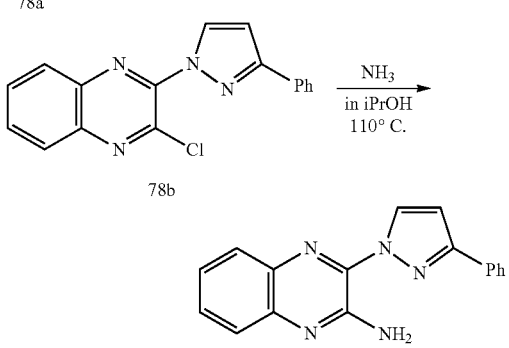

Step A—Synthesis of Compound 78b

To 3-phenyl-1H-pyrazole (188 mg, 1.3 mmol) in DMF (8 mL) was added NaH (60% in oil, 60 mg, 1.5 mmol) and the solution was stirred for 5 min. To the solution was added compound 78a (200 mg, 1.0 mmol) and the solution was heated to 60° C. for 1 h. Allowed to cool, concentrated under vacuum, and purified by preparative TLC (30% EtOAc/hexanes) to yield compound 78b (61 mg, 20%).

Step B—Synthesis of Compound 78

Using Step C from Example 2, substituting compound 78b for compound 2c, compound 78 was prepared.

Example 79

Preparation of Compound 79

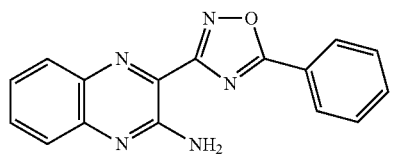

Using Step A from Example 62, substituting benzoyl chloride for phenylacetyl chloride, compound 79 was prepared.

Example 80

Preparation of Compound 80

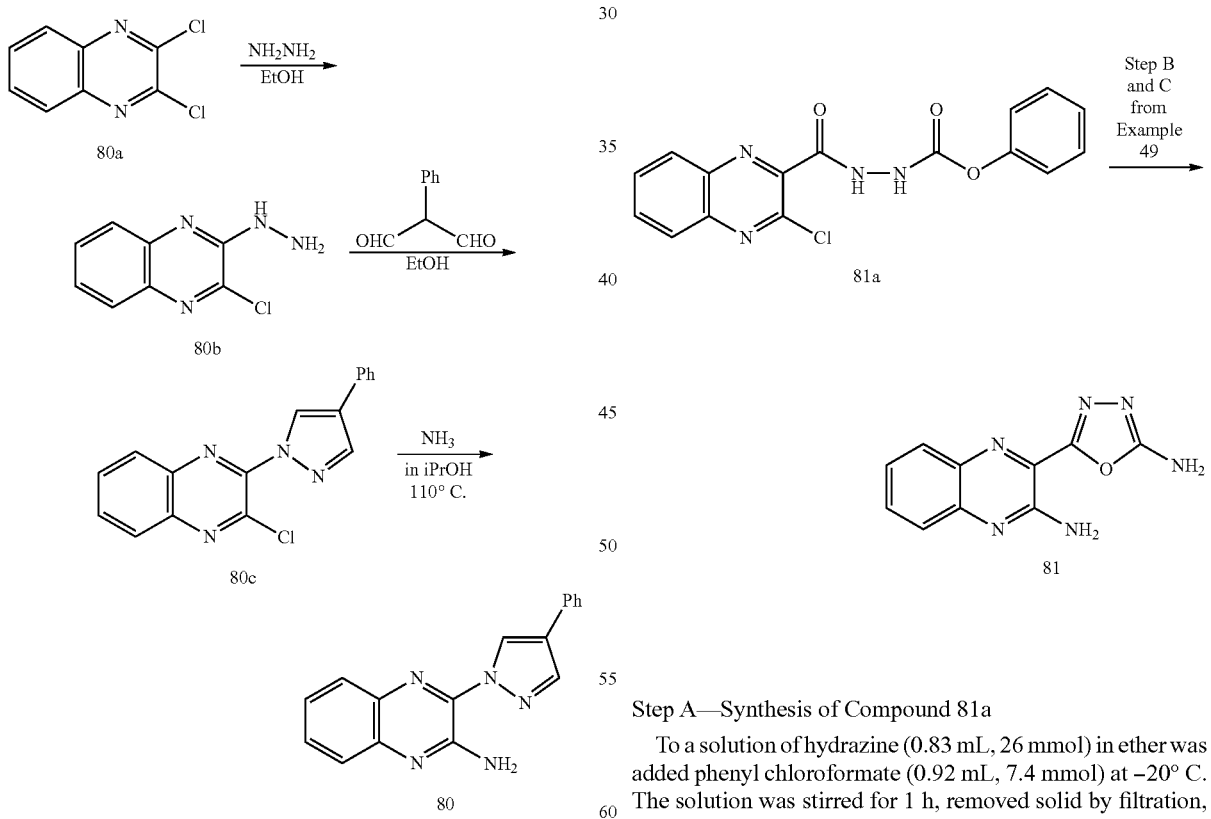

Step A—Synthesis of Compound 80b

To compound 80a (7.6 g, 38 mmol) were added EtOH (125 mL) and hydrazine hydrate (5.6 mL, 114 mmol) and the solution was stirred for 24 h. Filtered solid, rinsed with EtOH, and dried to yield compound 80b (3.7 g, 50%).

Step B—Synthesis of Compound 80c

To compound 80b (100 mg, 0.52 mmol) were added EtOH (6 mL) and 2-phenylmalondialdehyde (76 mg, 0.52 mmol) and the solution was stirred for 1 h. The reaction was concentrated and triturated with MeOH to yield compound 80c (90 mg, 57%).

Step C—Synthesis of Compound 80

Using Step C from Example 2, substituting compound 80c for compound 2c, compound 80 was prepared.

Example 81

Preparation of Compound 81

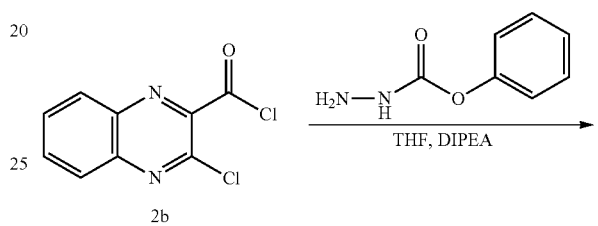

Step A—Synthesis of Compound 81a

To a solution of hydrazine (0.83 mL, 26 mmol) in ether was added phenyl chloroformate (0.92 mL, 7.4 mmol) at −20° C. The solution was stirred for 1 h, removed solid by filtration, and filtrate was concentrated to give phenyl hydrazinecarboxylate. To phenyl hydrazinecarboxylate was added compound 2b (1.2 g, 5.2 mmol), THF (20 mL), and DIPEA (1.5 mL) and the solution was stirred for 1 h. Partitioned reaction between sat. aq. NaHCO$_3$ and CH$_2$Cl$_2$, dried (MgSO$_4$), filtered, and concentrated to yield compound 81a (400 mg, 22%).

Step B—Synthesis of Compound 81

Using Steps B and C from Example 49, substituting compound 81a for compound 49b, compound 81 was prepared.

Example 82

Preparation of Compound 82

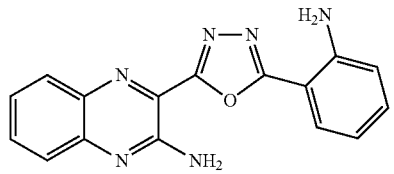

Using Steps A, B, and C from Example 49, substituting 2-aminobenzohydrazide for 2-methoxybenzohydrazide, compound 82 was prepared.

Example 83

Preparation of Compound 83

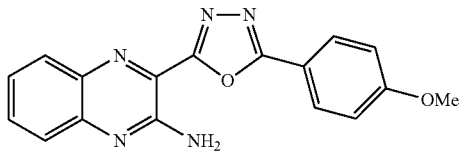

Using Steps A, B, and C from Example 49, substituting 4-methoxybenzohydrazide for 2-methoxybenzohydrazide, compound 83 was prepared.

Example 84

Preparation of Compound 84

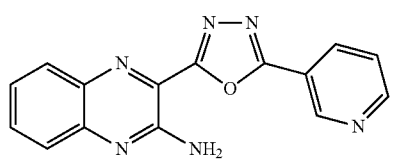

Using Steps A, B, and C from Example 49, substituting nicotinohydrazide for 2-methoxybenzohydrazide, compound 84 was prepared.

Example 85

Preparation of Compound 85

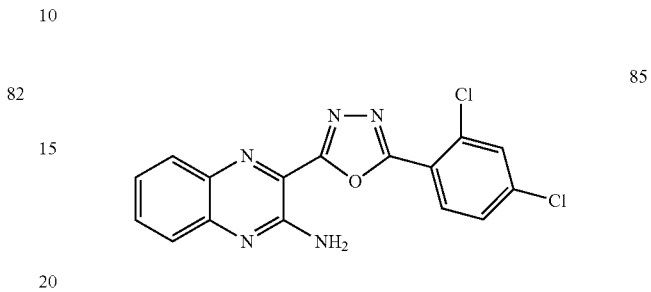

Using Steps A, B, and C from Example 49, substituting 2,4-dichlorobenzohydrazide for 2-methoxybenzohydrazide, compound 85 was prepared.

Example 86

Preparation of Compound 87

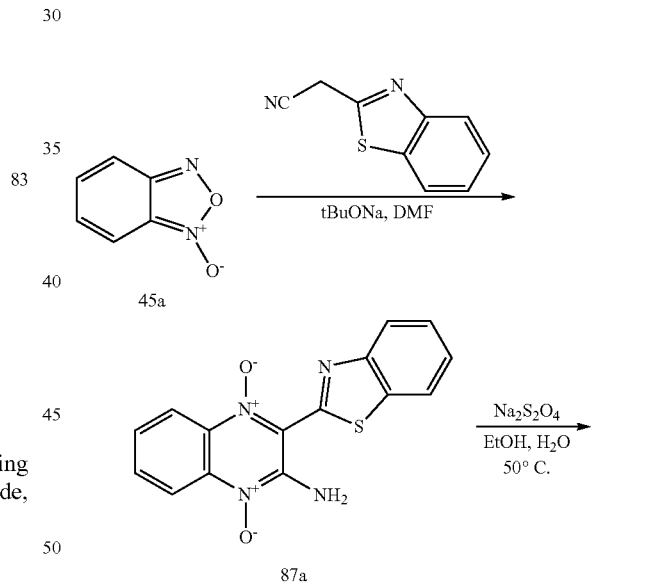

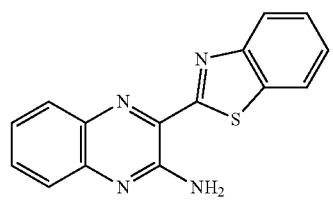

Using Step A from Example 45, substituting benzothiazole-2-acetonitrile for malononitrile and substituting NaOtBu for Et$_3$N, compound 87a was prepared. Using Step B from Example 45, substituting compound 87a for compound 45b, compound 87 was prepared.

Example 87

LC/MS Data For Selected Compounds

LC/MS data for selected Amino-Quinoxalines and Related Heterocyclic derivatives is provided below in Table 1, wherein the compound numbers correspond to the compound numbering set forth in the above specification.

TABLE 1

LC/MS Data For Selected Amino-Quinoxalines and Related Heterocyclic Derivatives

| Compound No. | Compound Name | LCMS Calculated M + 1 | LCMS Observed M + 1 |
|---|---|---|---|
| 1 | 3-AMINO-N-[(2,6-DICHLOROPHENYL)METHYL]-2-QUINOXALINECARBOXAMIDE | 347 | 347.2 |
| 2 | 3-AMINO-N-[(2-CHLORO-6-METHYLPHENYL)METHYL]-2-QUINOXALINECARBOXAMIDE | 327.1 | 327.1 |
| 3 | 3-AMINO-N-[(2,6-DIFLUOROPHENYL)METHYL]-2-QUINOXALINECARBOXAMIDE | 315.1 | 315.2 |
| 4 | 3-AMINO-N-(2,3-DIHYDRO-1H-INDEN-1(R)-YL)-2-QUINOXALINECARBOXAMIDE | 305.3 | 305.2 |
| 5 | 3-AMINO-N-[(2,6-DIFLUOROPHENYL)METHYL]-6,7-DIFLUORO-2-QUINOXALINECARBOXAMIDE | 351 | 351 |
| 6 | 3-AMINO-N-[[2-(METHYLTHIO)PHENYL]METHYL]-2-QUINOXALINECARBOXAMIDE | 325.1 | 325.2 |
| 7 | METHYL 2-[[[(3-AMINO-2-QUINOXALINYL)CARBONYL]AMINO]METHYL]BENZOATE | 337.1 | 337.2 |
| 8 | 3-AMINO-N-(1-NAPHTHALENYLMETHYL)-2-QUINOXALINECARBOXAMIDE | 329.4 | 329.2 |
| 9 | 3-AMINO-N-[(2-METHOXYPHENYL)METHYL]-2-QUINOXALINECARBOXAMIDE | 309.3 | 309.2 |
| 10 | 3-AMINO-N-(2,3-DIHYDRO-1H-INDEN-1-YL)-2-QUINOXALINECARBOXAMIDE | 305.3 | 305.2 |
| 11 | 3-AMINO-N-[[2-(TRIFLUOROMETHYL)PHENYL]METHYL]-2-QUINOXALINECARBOXAMIDE | 347.1 | 347.2 |
| 12 | 3-AMINO-N-[(2,3-DIFLUOROPHENYL)METHYL]-2-QUINOXALINECARBOXAMIDE | 315.1 | 315.2 |
| 13 | 3-AMINO-N-[[2-(HYDROXYMETHYL)PHENYL]METHYL]-2-QUINOXALINECARBOXAMIDE | 309.3 | 309.2 |
| 14 | 3-AMINO-N-[[2-(1-HYDROXY-1-METHYLETHYL)PHENYL]METHYL]-2-QUINOXALINECARBOXAMIDE | 337.4 | 337.2 |
| 15 | 3-AMINO-N-(PHENYLMETHYL)-2-QUINOXALINECARBOXAMIDE | 279.1 | 279.2 |
| 16 | 3-AMINO-6,7-DIFLUORO-N-[[2-(TRIFLUOROMETHYL)PHENYL]METHYL]-2-QUINOXALINECARBOXAMIDE | 383 | 383 |
| 17 | 3-AMINO-N-[[1,1'-BIPHENYL]-2-YLMETHYL]-2-QUINOXALINECARBOXAMIDE | 355.2 | 355.2 |
| 18 | 3-AMINO-N-(2-PYRIDINYLMETHYL)-2-QUINOXALINECARBOXAMIDE | 280.1 | 280.2 |
| 19 | 3-AMINO-N-[[2-[(METHYLSULFONYL)METHYL]PHENYL]METHYL]-2-QUINOXALINECARBOXAMIDE | 371.4 | 371.2 |
| 20 | 3-AMINO-N-(2-THIAZOLYLMETHYL)-2-QUINOXALINECARBOXAMIDE | 286.1 | 286.2 |
| 21 | 3-AMINO-N-[[3-(TRIFLUOROMETHYL)PHENYL]METHYL]-2-QUINOXALINECARBOXAMIDE | 347.1 | 347.2 |
| 22 | 3-AMINO-6,7-DIFLUORO-N-(PHENYLMETHYL)-2-QUINOXALINECARBOXAMIDE | 315 | 315 |
| 23 | 3-AMINO-N-[(2-AMINOPHENYL)METHYL]-2-QUINOXALINECARBOXAMIDE | 294.1 | 294.2 |
| 24 | 3-AMINO-N-[(2-NITROPHENYL)METHYL]-2-QUINOXALINECARBOXAMIDE | 324.1 | 324.2 |
| 25 | 3-AMINO-N-(2,3-DIHYDRO-1H-INDEN-1(S)-YL)-2-QUINOXALINECARBOXAMIDE | 305.3 | 305.2 |
| 26 | 1,1-DIMETHYLETHYL 2-[[[(3-AMINO-2-QUINOXALINYL)CARBONYL]AMINO]METHYL]PHENYL]CARBAMATE | 394.2 | 394.2 |

TABLE 1-continued

LC/MS Data For Selected Amino-Quinoxalines and Related Heterocyclic Derivatives

| Compound No. | Compound Name | LCMS Calculated M + 1 | LCMS Observed M + 1 |
|---|---|---|---|
| 27 | 3-AMINO-N-[[2-(METHYLSULFONYL)PHENYL]METHYL]-2-QUINOXALINECARBOXAMIDE | 357.4 | 357.2 |
| 28 | 3-AMINO-N-[(4-FLUOROPHENYL)METHYL]-2-QUINOXALINECARBOXAMIDE | 297.1 | 297.2 |
| 29 | 3-AMINO-N-(1,3-BENZODIOXOL-5-YLMETHYL)-2-QUINOXALINECARBOXAMIDE | 323.1 | 323.2 |
| 30 | 3-AMINO-N-[(3,5-DIFLUOROPHENYL)METHYL]-2-QUINOXALINECARBOXAMIDE | 315.1 | 315.2 |
| 31 | 3-AMINO-N-(2,3-DIHYDRO-2(R)-HYDROXY-1H-INDEN-1(S)-YL)-2-QUINOXALINECARBOXAMIDE | 321.3 | 321.2 |
| 32 | 3-AMINO-N-(1,2,3,4-TETRAHYDRO-1-NAPHTHALENYL)-2-QUINOXALINECARBOXAMIDE | 319.4 | 319.2 |
| 33 | 3-AMINO-N-[[4-(TRIFLUOROMETHYL)PHENYL]METHYL]-2-QUINOXALINECARBOXAMIDE | 347.1 | 347.2 |
| 34 | 3-AMINO-N-[[1,1'-BIPHENYL]-3-YLMETHYL]-2-QUINOXALINECARBOXAMIDE | 355.2 | 355.2 |
| 35 | 3-AMINO-N-(PHENYLMETHYL)-6-(TRIFLUOROMETHYL)-2-QUINOXALINECARBOXAMIDE | 347 | 347 |
| 36 | METHYL 3-[[[(3-AMINO-2-QUINOXALINYL)CARBONYL]AMINO]METHYL]BENZOATE | 337.1 | 337.2 |
| 37 | 3-AMINO-N-(3-PYRIDINYLMETHYL)-2-QUINOXALINECARBOXAMIDE | 280.1 | 280.2 |
| 38 | 3-AMINO-N-(1-PHENYLETHYL)-2-QUINOXALINECARBOXAMIDE | 293.3 | 293.2 |
| 39 | 3-AMINO-N-[[3-(METHYLSULFONYL)PHENYL]METHYL]-2-QUINOXALINECARBOXAMIDE | 357.1 | 357.2 |
| 40 | N-[[3-[ACETYL(METHYL)AMINO]PHENYL]METHYL]-3-AMINO-2-QUINOXALINECARBOXAMIDE | 350.2 | 350.2 |
| 41 | 3-AMINO-N-[(4-METHOXYPHENYL)METHYL]-2-QUINOXALINECARBOXAMIDE | 309.1 | 309.2 |
| 42 | 3-AMINO-N-(2-PHENOXYETHYL)-2-QUINOXALINECARBOXAMIDE | 309.1 | 309.2 |
| 43 | 3-AMINO-2-QUINOXALINECARBOXAMIDE | 189.1 | 189.1 |
| 44 | 3-AMINO-N-(2-PHENYLETHYL)-2-QUINOXALINECARBOXAMIDE | 292.1 | 293.2 |
| 45 | 3-AMINO-2-QUINOXALINECARBONITRILE | 171.1 | 171.1 |
| 46 | 2-AMINO-N-(PHENYLMETHYL)-3-QUINOLINECARBOXAMIDE | 278.3 | 278.1 |
| 47 | 3-AMINO-N'-HYDROXY-2-QUINOXALINECARBOXIMIDAMIDE | 204 | 204 |
| 48 | N-[[3-(ACETYLAMINO)PHENYL]METHYL]-3-AMINO-2-QUINOXALINECARBOXAMIDE | 336.1 | 336.2 |
| 49 | 3-[5-(2-METHOXYPHENYL)-1,3,4-OXADIAZOL-2-YL]-2-QUINOXALINAMINE | 320.1 | 320.2 |
| 50 | 3-[5-[2-(TRIFLUOROMETHYL)PHENYL]-1,3,4-OXADIAZOL-2-YL]-2-QUINOXALINAMINE | 358.1 | 358.2 |
| 51 | 3-[5-(PHENYLMETHYL)-1,3,4-OXADIAZOL-2-YL]-2-QUINOXALINAMINE | 304.1 | 304.1 |
| 52 | 3-[5-[[2-(TRIFLUOROMETHYL)PHENYL]METHYL]-1,3,4-OXADIAZOL-2-YL]-2-QUINOXALINAMINE | 372 | 372 |
| 53 | 3-[5-[(2,6-DIFLUOROPHENYL)METHYL]-1,3,4-OXADIAZOL-2-YL]-2-QUINOXALINAMINE | 340 | 340 |
| 54 | 3-[5-(2-METHYLPHENYL)-1,3,4-OXADIAZOL-2-YL]-2-QUINOXALINAMINE | 304.1 | 304.2 |
| 55 | 3-[5-[2-(TRIFLUOROMETHOXY)PHENYL]-1,3,4-OXADIAZOL-2-YL]-2-QUINOXALINAMINE | 374 | 374 |
| 56 | 3-[5-(2-CHLOROPHENYL)-1,3,4-OXADIAZOL-2-YL]-2-QUINOXALINAMINE | 324.1 | 324.2 |
| 57 | 3-[5-(2-FLUOROPHENYL)-1,3,4-OXADIAZOL-2-YL]-2-QUINOXALINAMINE | 308.1 | 308.2 |
| 58 | 3-(5-PHENYL-1,3,4-OXADIAZOL-2-YL)-2-QUINOXALINAMINE | 290.1 | 290.2 |
| 59 | 3-[5-(2-PYRIDINYL)-1,3,4-OXADIAZOL-2-YL]-2-QUINOXALINAMINE | 291.1 | 291.2 |
| 60 | 3-[5-(2,6-DIFLUOROPHENYL)-1,3,4-OXADIAZOL-2-YL]-2-QUINOXALINAMINE | 326.1 | 326.2 |
| 61 | 3-[5-(2-THIENYL)-1,3,4-OXADIAZOL-2-YL]-2-QUINOXALINAMINE | 296.1 | 296.2 |

TABLE 1-continued

LC/MS Data For Selected Amino-Quinoxalines and Related Heterocyclic Derivatives

| Compound No. | Compound Name | LCMS Calculated M + 1 | LCMS Observed M + 1 |
|---|---|---|---|
| 62 | 3-[5-(PHENYLMETHYL)-1,2,4-OXADIAZOL-3-YL]-2-QUINOXALINAMINE | 304 | 304 |
| 63 | N-[2-[5-(3-AMINO-2-QUINOXALINYL)-1,3,4-OXADIAZOL-2-YL]PHENYL]METHANESULFONAMIDE | 383.1 | 383.2 |
| 64 | 3-[5-(3-FLUOROPHENYL)-1,3,4-OXADIAZOL-2-YL]-2-QUINOXALINAMINE | 308.1 | 308.2 |
| 65 | 3-[5-[2-(METHYLSULFONYL)PHENYL]-1,3,4-OXADIAZOL-2-YL]-2-QUINOXALINAMINE | 368.1 | 368.2 |
| 66 | 3-[5-(2,5-DICHLOROPHENYL)-1,3,4-OXADIAZOL-2-YL]-2-QUINOXALINAMINE | 358 | 358.2 |
| 67 | METHYL [2-[5-(3-AMINO-2-QUINOXALINYL)-1,3,4-OXADIAZOL-2-YL]PHENYL]CARBAMATE | 363.1 | 363.2 |
| 68 | 3-[5-(4-FLUOROPHENYL)-1,3,4-OXADIAZOL-2-YL]-2-QUINOXALINAMINE | 308.1 | 308.2 |
| 69 | 3-[5-(2-NITROPHENYL)-1,3,4-OXADIAZOL-2-YL]-2-QUINOXALINAMINE | 335.1 | 335.2 |
| 70 | 3-[3-(PHENYLMETHYL)-1,2,4-OXADIAZOL-5-YL]-2-QUINOXALINAMINE | 304 | 304 |
| 71 | 3-[5-(3-METHOXYPHENYL)-1,3,4-OXADIAZOL-2-YL]-2-QUINOXALINAMINE | 320.1 | 320.2 |
| 72 | 3-[5-(3,4-DIFLUOROPHENYL)-1,3,4-OXADIAZOL-2-YL]-2-QUINOXALINAMINE | 326.1 | 326.2 |
| 73 | N-[2-[5-(3-AMINO-2-QUINOXALINYL)-1,3,4-OXADIAZOL-2-YL]PHENYL]ACETAMIDE | 347.1 | 347.2 |
| 74 | 6,7-DIFLUORO-3-(5-PHENYL-1,3,4-OXADIAZOL-2-YL)-2-QUINOXALINAMINE | 326.3 | 326.2 |
| 75 | 3-[5-(PHENYLAMINO)-1,3,4-OXADIAZOL-2-YL]-2-QUINOXALINAMINE | 305.1 | 305.2 |
| 76 | 3-[5-[3-(TRIFLUOROMETHYL)PHENYL]-1,3,4-OXADIAZOL-2-YL]-2-QUINOXALINAMINE | 358.1 | 358.2 |
| 77 | 3-(5-PHENYL-2-OXAZOLYL)-2-QUINOXALINAMINE | 289 | 289 |
| 78 | 3-(3-PHENYL-1H-PYRAZOL-1-YL)-2-QUINOXALINAMINE | 288.3 | 288.2 |
| 79 | 3-(5-PHENYL-1,2,4-OXADIAZOL-3-YL)-2-QUINOXALINAMINE | 290 | 290 |
| 80 | 3-(4-PHENYL-1H-PYRAZOL-1-YL)-2-QUINOXALINAMINE | 288.3 | 288.2 |
| 81 | 3-(5-AMINO-1,3,4-OXADIAZOL-2-YL)-2-QUINOXALINAMINE | 229.1 | 229.1 |
| 82 | 3-[5-(2-AMINOPHENYL)-1,3,4-OXADIAZOL-2-YL]-2-QUINOXALINAMINE | 305.1 | 305.2 |
| 83 | 3-[5-(4-METHOXYPHENYL)-1,3,4-OXADIAZOL-2-YL]-2-QUINOXALINAMINE | 320.2 | 320.2 |
| 84 | 3-[5-(3-PYRIDINYL)-1,3,4-OXADIAZOL-2-YL]-2-QUINOXALINAMINE | 291.1 | 291.2 |
| 85 | 3-[5-(2,4-DICHLOROPHENYL)-1,3,4-OXADIAZOL-2-YL]-2-QUINOXALINAMINE | 358 | 358.2 |
| 86 | N-[3-[5-(PHENYLMETHYL)-1,2,4-OXADIAZOL-3-YL]-2-QUINOXALINYL]BENZENEACETAMIDE | 422 | 422 |
| 87 | 3-(2-BENZOTHIAZOLYL)-2-QUINOXALINAMINE | 279 | 279 |

Because of their adenosine $A_{2a}$ receptor antagonist activity, compounds of the present invention are useful in the treatment of depression, cognitive function diseases and neurodegenerative diseases such as Parkinson's disease, senile dementia as in Alzheimer's disease, psychoses of organic origin, attention deficit disorders, EPS, dystonia, RLS and PLMS. In particular, the compounds of the present invention can improve motor-impairment due to neurodegenerative diseases such as Parkinson's disease.

The other agents known to be useful in the treatment of Parkinson's disease that can be administered in combination with the compounds of Formula I include: L-DOPA; dopaminergic agonists such as quinpirole, ropinirole, pramipexole, pergolide and bromocriptine; MAO-B inhibitors such as deprenyl and selegiline; DOPA decarboxylase inhibitors such as carbidopa and benserazide; and COMT inhibitors such as tolcapone and entacapone.

In this specification, the term "at least one compound of Formula I" (or a pharmaceutically acceptable salt, solvate, ester or prodrug thereof) means that one to three different compounds of Formula I (or pharmaceutically acceptable salt, solvate, ester or prodrug thereof) may be used in a pharmaceutical composition or method of treatment. Preferably one compound of Formula I or pharmaceutically acceptable salt, solvate, ester or prodrug thereof is used. Similarly, "one or more agents useful in the treatment of Parkinson's disease" means that one to three different agents, preferably one agent, may be used in a pharmaceutical composition or method of treatment. Preferably, one agent is used in combination with one compound of Formula I or pharmaceutically acceptable salt, solvate, ester or prodrug thereof.

The pharmacological activity of the compounds of the invention was determined by the following in vitro assays to measure $A_{2a}$ receptor activity.

Human Adenosine $A_{2a}$ and $A_1$ Receptor Competition Binding Assay Protocol

Membrane Sources:

$A_{2a}$: Human $A_{2a}$ Adenosine Receptor membranes, Catalog #RB-HA2a, Receptor Biology, Inc., Beltsville, Md. Dilute to 17 µg/100 µl in membrane dilution buffer (see below).

Assay Buffers:

Membrane dilution buffer: Dulbecco's Phosphate Buffered Saline (Gibco/BRL)+10 mM $MgCl_2$.

Compound Dilution Buffer: Dulbecco's Phosphate Buffered Saline (Gibco/BRL)+10 mM $MgCl_2$ supplemented with 1.6 mg/ml methyl cellulose and 16% DMSO. Prepared fresh daily.

Ligands:

$A_{2a}$: [3H]-SCH 58261, custom synthesis, Amersham Pharmacia Biotech, Piscataway, N.J. Stock is prepared at 1 nM in membrane dilution buffer. Final assay concentration is 0.5 nM.

$A_1$: [3H]-DPCPX, Amersham Pharmacia Biotech, Piscataway, N.J. Stock is prepared at 2 nM in membrane dilution buffer. Final assay concentration is 1 nM.

Non-specific Binding:

$A_{2a}$: To determine non-specific binding, add 100 nM CGS 15923 (RBI, Natick, Mass.). Working stock is prepared at 400 nM in compound dilution buffer.

$A_1$: To determine non-specific binding, add 100 µM NECA (RBI, Natick, Mass.). Working stock is prepared at 400 µM in compound dilution buffer.

Compound Dilution:

Prepare 1 mM stock solutions of compounds in 100% DMSO. Dilute in compound dilution buffer. Test at 10 concentrations ranging from 3 µM to 30 µM. Prepare working solutions at 4× final concentration in compound dilution buffer.

Assay Procedure:

Perform assays in deep well 96 well plates. Total assay volume is 200 µl. Add 50 µl compound dilution buffer (total ligand binding) or 50 µl CGS 15923 working solution ($A_{2a}$ non-specific binding) or 50 µl NECA working solution ($A_1$ non-specific binding) or 50 µl of drug working solution. Add 50 µl ligand stock ([3H]-SCH 58261 for $A_{2a}$, [3H]-DPCPX for $A_1$). Add 100 µl of diluted membranes containing the appropriate receptor. Mix. Incubate at room temperature for 90 minutes. Harvest using a Brandel cell harvester onto Packard GF/B filter plates. Add 45 µl Microscint 20 (Packard), and count using the Packard TopCount Microscintillation Counter. Determine $IC_{50}$ values by fitting the displacement curves using an iterative curve fitting program (Excel). Determine $K_i$ values using the Cheng-Prusoff equation.

Using the above test procedures, the following results were obtained for preferred and/or representative compounds of the invention.

Results of the binding assay on compounds of the invention showed $A_{2a}$ $K_i$ values of 0.2 to 97.2 nM, with preferred compounds showing $K_i$ values between 0.2 and 5.0 nM. Selectivity is determined by dividing $K_i$ for $A_1$ receptor by $K_i$ for $A_2$ receptor. Preferred compounds of the invention have a selectivity ranging from about 100 to about 1500.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen for compounds of formula I is oral administration of from 10 mg to 2000 mg/day preferably 10 to 1000 mg/day, in two to four divided doses to provide relief from central nervous system diseases such as Parkinson's disease or the other disease or conditions listed above.

The doses and dosage regimen of the dopaminergic agents will be determined by the attending clinician in view of the approved doses and dosage regimen in the package insert, taking into consideration the age, sex and condition of the patient and the severity of the disease. It is expected that when the combination of a compound of Formula I and a dopaminergic agent is administered, lower doses of the components will be effective compared to the doses of the components administered as monotherapy.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the structural Formula I:

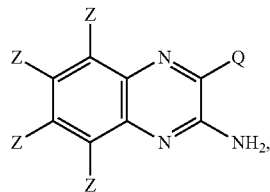

I or a pharmaceutically acceptable salt thereof, wherein:
Z is independently hydrogen, halogen or haloalkyl;
Q is —CONHR¹; or is a heterocyclic radical selected from the group consisting of:

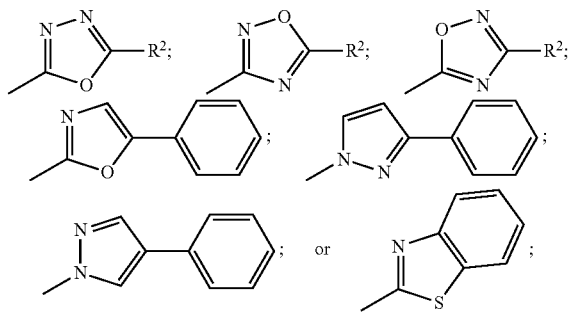

R¹ is aralkyl, aryloxyalkyl, benzocycloalkyl or heteroarylalkyl; and
R² is amino, aryl, heteroaryl, arylamino, arylalkyl or heteroarylalkyl.

2. The compound of claim 1, or a pharmaceutically acceptable salt thereof, wherein Q is a heterocyclic radical of the formula:

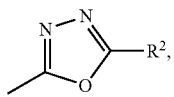

wherein R² is amino, aryl, heteroaryl, arylamino, arylalkyl or heteroarylalkyl.

3. A compound of the structure:

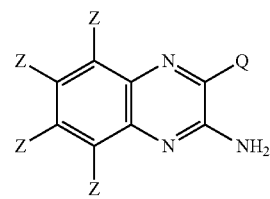

or a pharmaceutically acceptable salt thereof, wherein:
Z is independently hydrogen, halogen or haloalkyl;
Q is independently —CONHR¹ or a heterocyclic radical of the formula:

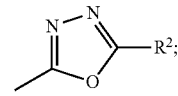

wherein:
R¹ is aralkyl, benzocycloalkyl or heteroarylalkyl; and
R² is aryl, heteroaryl or arylalkyl.

4. The compound of claim 3, or a pharmaceutically acceptable salt thereof, wherein Q is —CONHR¹.

5. A pharmaceutical composition comprising at least one compound of claim 3, or a pharmaceutically acceptable salt thereof and at least one pharmaceutically acceptable carrier, adjuvant or vehicle.

6. A compound selected from the group consisting of:

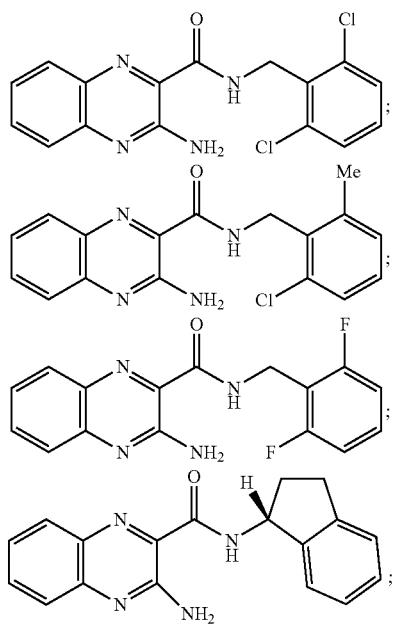

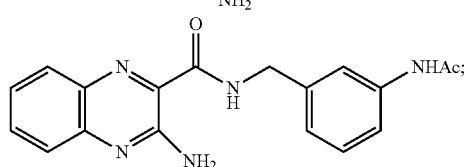

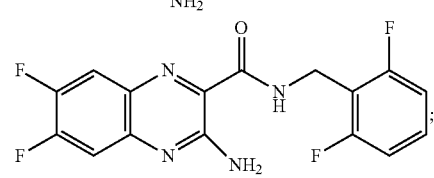

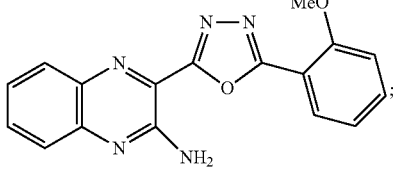

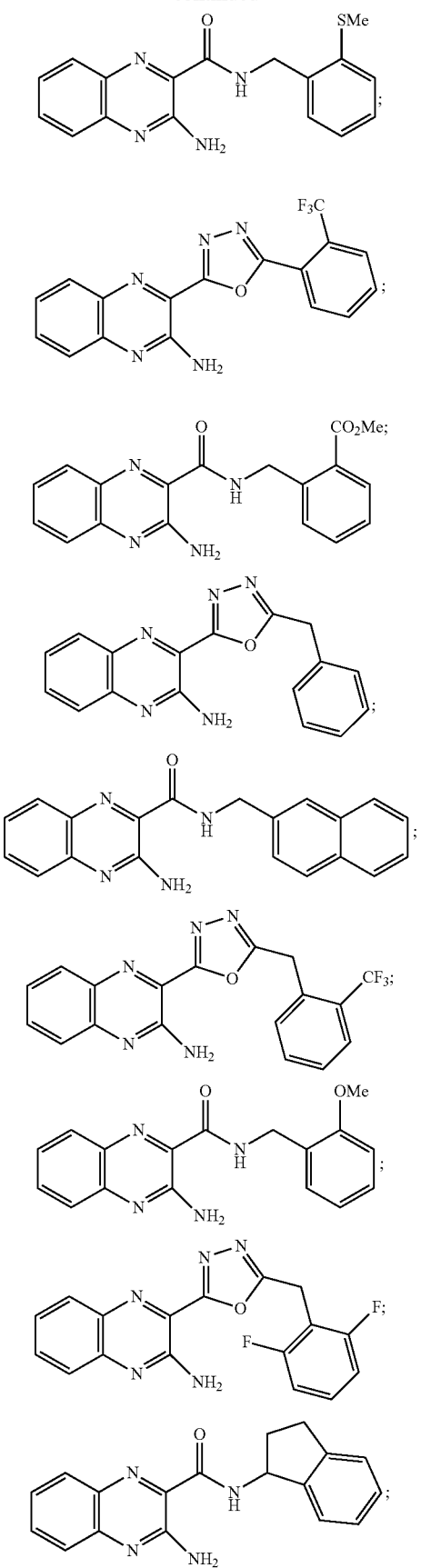
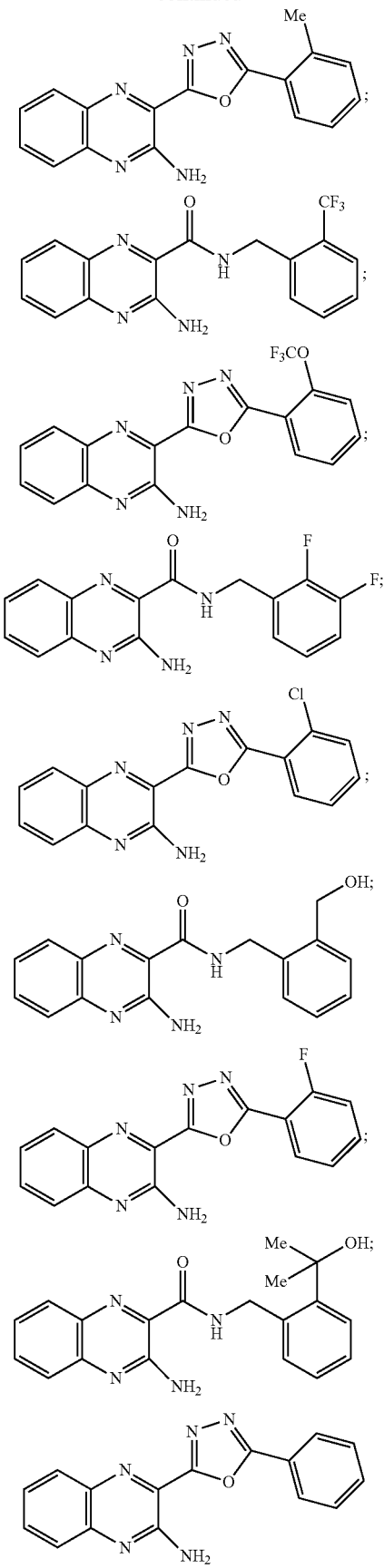

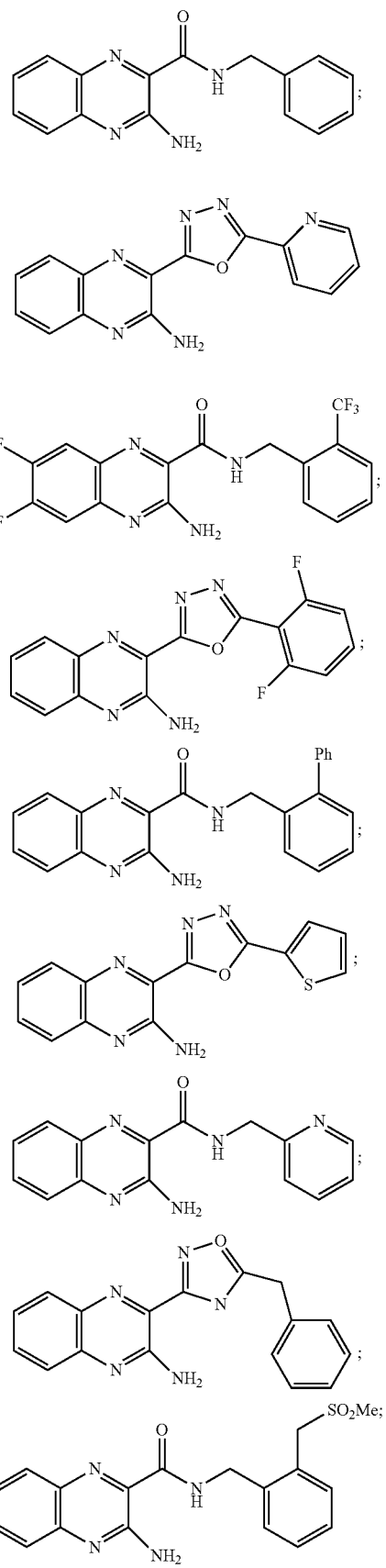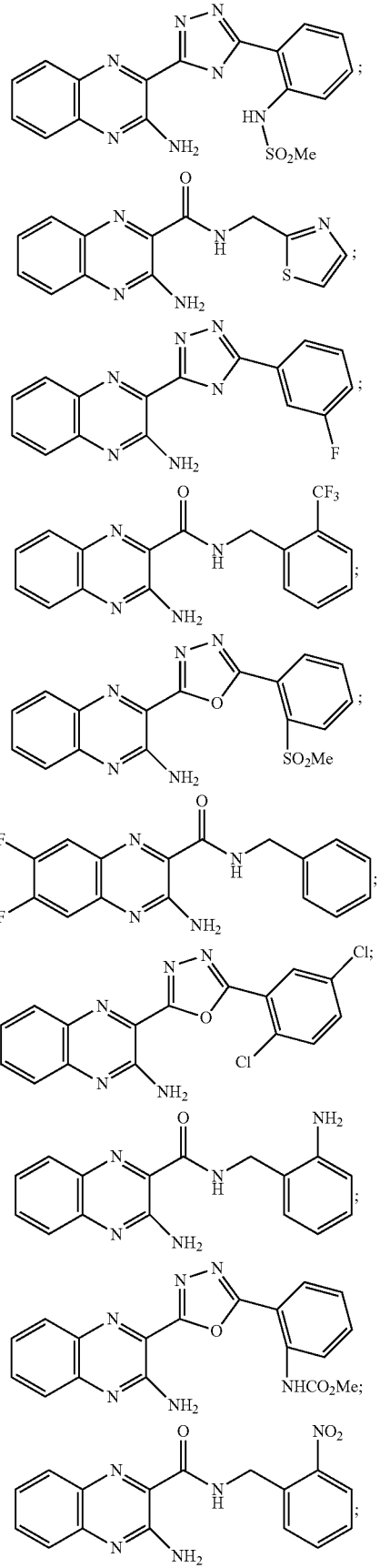

-continued
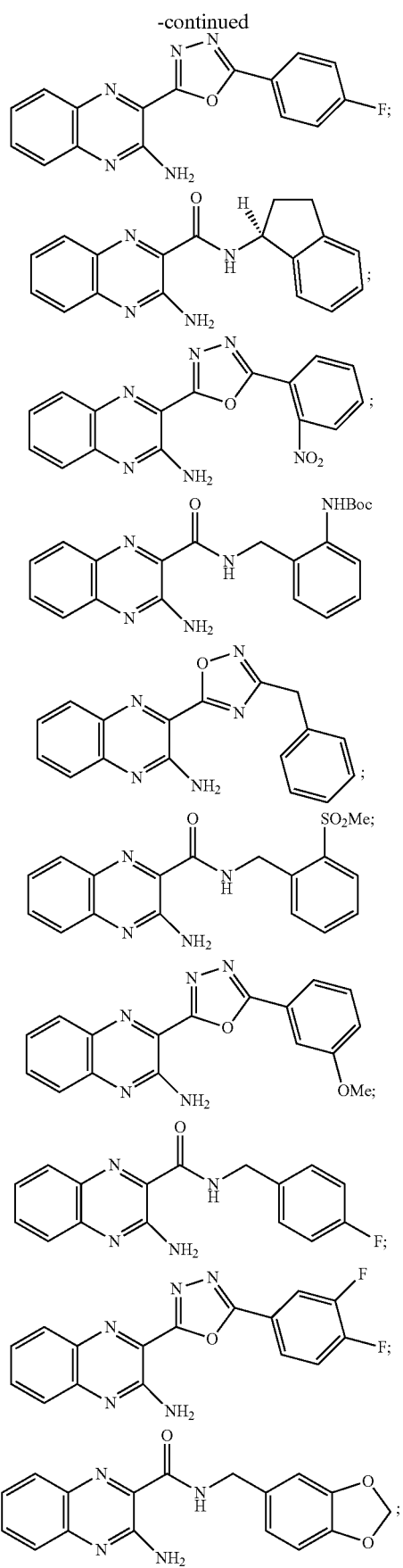
-continued
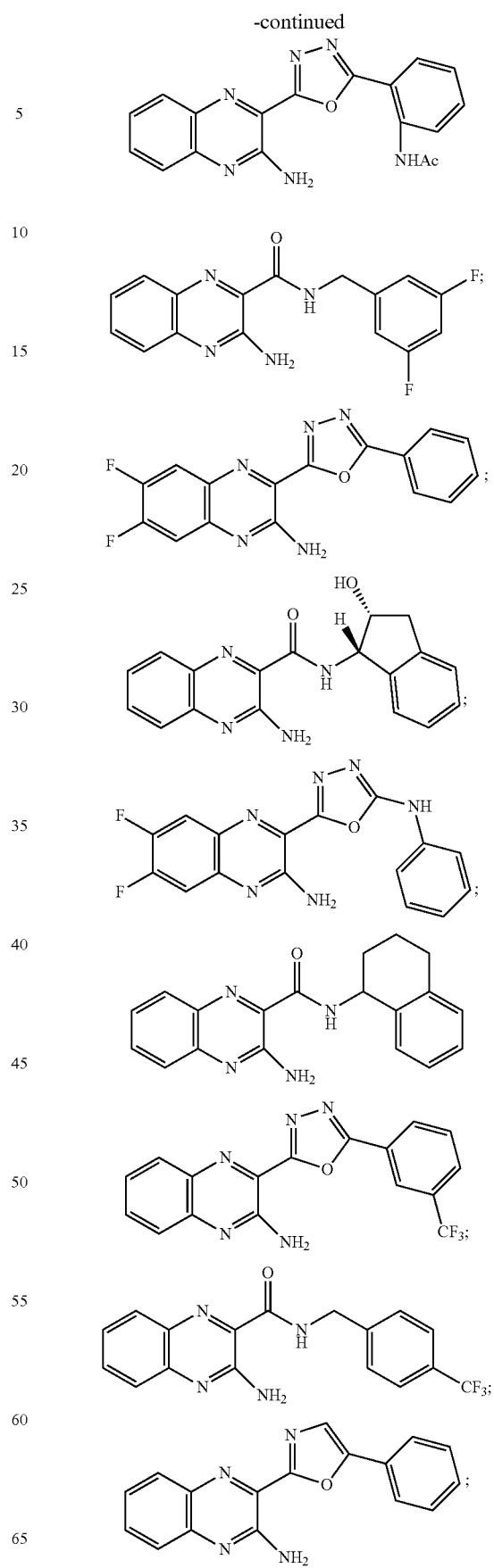

-continued
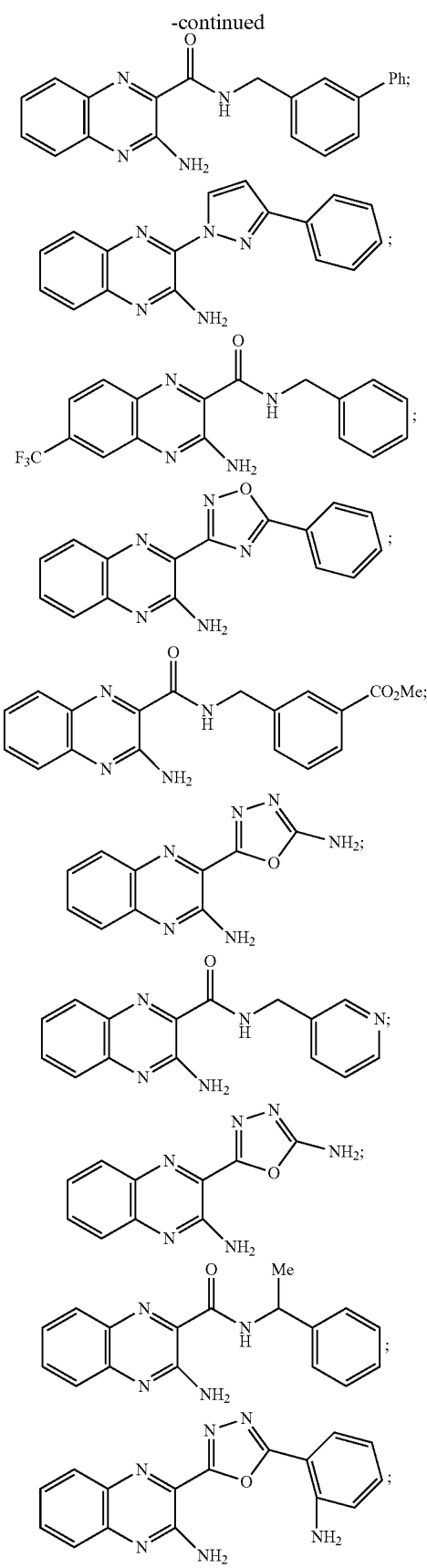
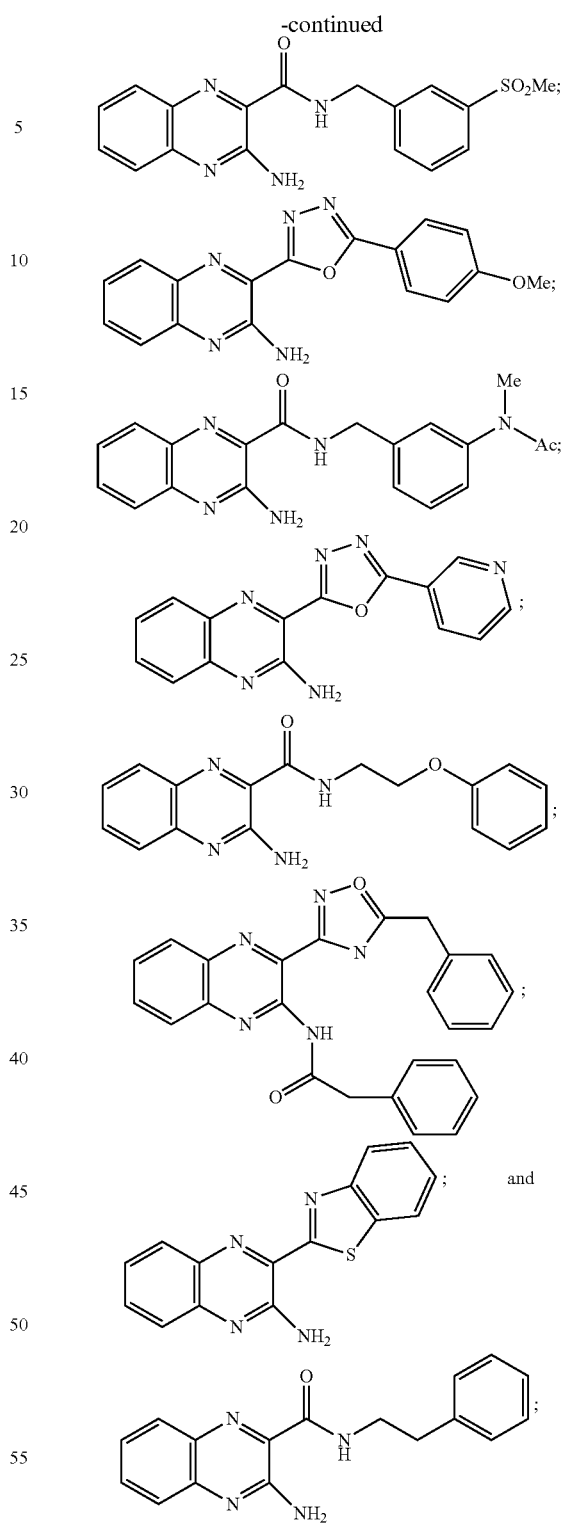
or a pharmaceutically acceptable salt thereof.
7. A pharmaceutical composition comprising at least one compound of claim 6, or a pharmaceutically acceptable salt-thereof and at least one pharmaceutically acceptable carrier, adjuvant or vehicle.
* * * * *

UNITED STATES PATENT AND TRADEMARK OFFICE
CERTIFICATE OF CORRECTION

| | | |
|---|---|---|
| PATENT NO. | : 8,415,353 B2 | Page 1 of 1 |
| APPLICATION NO. | : 12/920928 | |
| DATED | : April 9, 2013 | |
| INVENTOR(S) | : Harris et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 45 days.

Signed and Sealed this
Thirtieth Day of December, 2014

Michelle K. Lee
*Deputy Director of the United States Patent and Trademark Office*